(12) United States Patent
Greenwalt

(10) Patent No.: US 7,405,037 B2
(45) Date of Patent: Jul. 29, 2008

(54) METHODS AND TOOLS FOR DETECTING COLLAGEN DEGRADATION

(75) Inventor: Dale Greenwalt, Walkersville, MD (US)

(73) Assignee: Lonza Walkersville, Inc., Walkersville, MD (US)

( * ) Notice: Subject to any disclaimer, the term of this patent is extended or adjusted under 35 U.S.C. 154(b) by 254 days.

(21) Appl. No.: 10/840,653

(22) Filed: May 7, 2004

(65) Prior Publication Data

US 2005/0250171 A1     Nov. 10, 2005

(51) Int. Cl.
*C12Q 1/00* (2006.01)
*C12N 5/02* (2006.01)

(52) U.S. Cl. .......................................... 435/4; 435/325

(58) Field of Classification Search .................... 435/4, 435/325
See application file for complete search history.

(56) References Cited

U.S. PATENT DOCUMENTS

| | | | |
|---|---|---|---|
| 5,342,756 A | 8/1994 | Risteli et al. | |
| 5,538,853 A | 7/1996 | Risteli et al. | |
| 5,585,356 A * | 12/1996 | Liotta et al. | 514/17 |
| 6,346,373 B1 * | 2/2002 | Mancini et al. | 435/4 |
| 6,468,808 B1 | 10/2002 | Nie et al. | |
| 2003/0166728 A1 * | 9/2003 | Shorr et al. | 514/569 |

OTHER PUBLICATIONS

Kaneko et al., "Alterations in peripheral concentrations of inhibin a in cattle studied using a time resolved immunofluorometric assay: relationship with estradiol and follicle stimulating hormone in various reproductice conditions", Biologyc of Reproduction, 2002 (67):38-45.*

Garbisa et al., "Quantitation of basement membrane collagen degradation by living tumor cells in vitro," *Cancer Letters 9*, 359-66, 1980.

Liotta et al., "Role of collagenases in tumor cell invasion," *Cancer Metastasis Reviews 1*, 277-88, 1982.

Stearns, "Alendronate blocks TGF-beta 1 stimulated collagen 1 degradation by human prostate PC-3 ML cells,"Clin Exp Metastasis. May 1998;16(4):332-9.

Osteometer BioTech A/S, "CrossLaps™ for Culture" (instructions for use), pp. 1-15, Jan. 2000.

Macklis et al., "Cross-Linked Collagen Surface for Cell Culture That is Stable, Uniform, and Optically Superior to Conventional Surfaces," *In Vitro Cellular & Devel. Biol. 21*, 189-94, Mar. 1985.

Gurdak et al., "Resolution of the Vertical and Horizontal Heterogeneity of Adsorbed Collagen Layers by Combination of QCM-D and AFM," *Langmuir 21*, 10684-92, web release date Sep. 27, 2005 (abstract).

Müller et al., "Surface engineering of stainless steel materials by covalent collagen immobilization to improve implant biocompatibility," *Biomaterials 26*, 6962-72, Dec. 1985 (abstract).

* cited by examiner

*Primary Examiner*—Ruth A Davis
(74) *Attorney, Agent, or Firm*—Banner & Witcoff, Ltd.

(57) ABSTRACT

Fluorophore-labeled collagen covalently bound to a cell culture vessel can be used to assay collagen degradation by a variety of cell types, including osteoclasts and tumor cells. Such assays provide a high throughput platform for rapid screening of large numbers of potential modulators of, for example, tumor metastasis or osteoclast differentiation and/or function.

20 Claims, 17 Drawing Sheets

US 7,405,037 B2

METHODS AND TOOLS FOR DETECTING COLLAGEN DEGRADATION

FIELD OF THE INVENTION

The invention relates to methods and tools for detecting collagen degradation.

BACKGROUND OF THE INVENTION

Collagen degradation is involved in a variety of processes, including bone resorption and tumor metastasis. In vitro assays of the collagen-degrading activity of osteoclasts, for example, are invaluable to the discovery of drugs for the treatment of osteoporosis. "TRAP" (tartrate-resistant acid phosphatase) assays detect acid phosphatase produced by mature osteoclasts via either histochemical or immunohistochemical staining. Other existing assays use synthetic calcium phosphate-based matrices as a surrogate bone substrate to detect osteoclast activity, and culture dishes coated with calcium phosphate upon which osteoclasts can be cultured are commercially available.

Some assays use slices of either dentine or bovine cortical bone as a surrogate bone substrate. Stearns, Clin Exp Metastasis. 1998 May; 16(4):332-9, discloses an assay in which osteoblasts first are cultured with $^3$H-hydroxyproline. The osteoblasts produce $^3$H-collagen, which is deposited together with other matrix proteins on a culture plate surface. The osteoblasts are removed, and other cells can then be tested for the ability to degrade the deposited $^3$H-collagen.

Tumor cells secrete collagenases which degrade extracellular matrix components and aid metastasis. Garbisa et al., *Cancer Lett.* 9, 359-66, 1980; Liotta et al., *Cancer Metastasis Reviews* 1, 277-88, 1982. Cell-based assays for potential drugs that would block this process would be useful in identifying anti-metastatic agents.

There is a need in the art for sensitive and convenient cell-based assays of collagen degradation that can be used for rapid screening of potential therapeutic agents.

BRIEF SUMMARY OF THE INVENTION

One embodiment of the invention is a method of detecting collagen degradation. Cells which can degrade collagen or can differentiate into cells which can degrade collagen are cultured in culture medium on fluorophore-labeled collagen covalently bound to a culture surface of a cell culture vessel. The presence or absence of a fluorescence signal is detected in a sample of the culture medium. Fluorescence signal intensity reflects the concentration of fluorophore-labeled collagen fragments in the sample of the culture medium.

Another embodiment of the invention is a method of detecting collagen degradation. Osteoclasts or osteoclast precursors are cultured in culture medium on fluorophore-labeled collagen covalently bound to a culture surface of a cell culture vessel. A sample of the culture medium is transferred from the cell culture vessel to an assay vessel. The presence or absence of a fluorescence signal is detected in the assay vessel. Fluorescence signal intensity reflects the concentration of fluorophore-labeled collagen fragments in the sample of the culture medium.

Yet another embodiment of the invention is a cell culture vessel comprising fluorophore-labeled collagen covalently bound to a culture surface of the cell culture vessel.

Still another embodiment of the invention is a cell culture vessel comprising europium chelate-labeled human collagen type I covalently bound to a culture surface of the cell culture vessel.

Other embodiments of the invention are kits for detecting collagen degradation. The kits contain cell culture vessels and instructions for carrying out methods of the invention.

The invention thus provides methods and tools for carrying out rapid and sensitive detection of collagen degradation.

BRIEF DESCRIPTION OF THE FIGURES

FIG. 4. Graphs showing effects of adding growth factors at day 7 [macrophage colony stimulating factor (M-CSF) and soluble receptor activator of NF-κB ligand (RANK ligand)] in an OsteoLyse™ Assay.

DETAILED DESCRIPTION OF THE INVENTION

Figure 1:
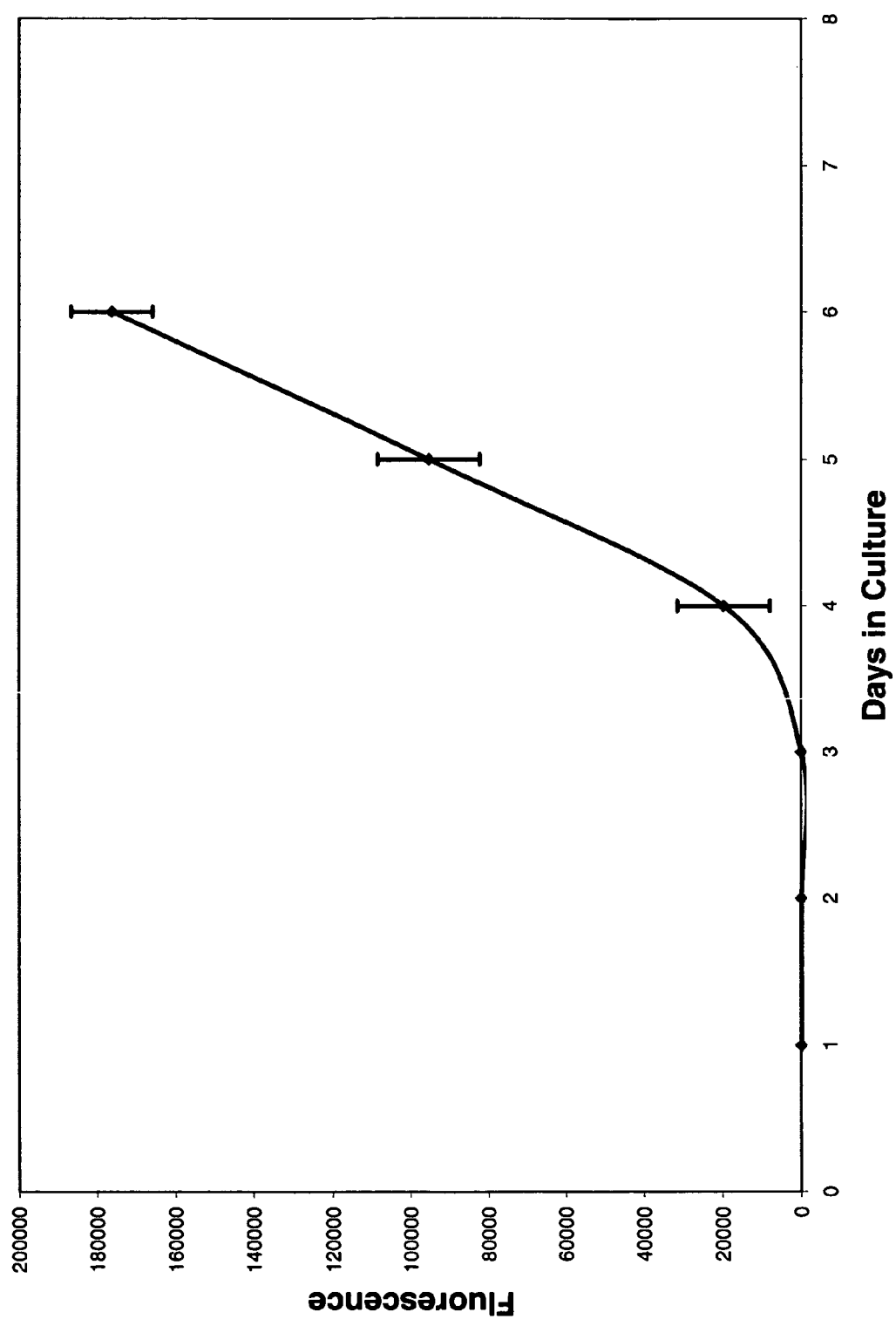
FIG. 1. Graph showing fluorescence resulting from the release over time of europium chelate-labeled degradation fragments of collagen from europium chelate-labeled collagen covalently bound to a maleic anhydride-derivatized polystyrene plate ("OsteoLyse™ plate") on which osteoclast precursors were cultured.

The present invention provides tools and methods for in vitro measurement of matrix (e.g., bone or extracellular matrix) collagen degradation in cell-based assays, including collagen degradation associated with bone resorption and tumor metastasis. Assays of the invention provide a high throughput platform for rapid screening of large numbers of compounds that potentially modulate, e.g. potentially activate or inhibit, for example, tumor metastasis or osteoclast differentiation and function. In fact, assays of the invention require much less time than currently available assays for examining bone resorption. In addition, data from such assays correlate very well with more traditional assays of osteoclast function, such as the TRAP assay (Janckila et al., Am J. Clin. Pathol. 70 (1):45-55, 1978), although assays of the invention are much more readily quantifiable and have a greatly increased throughput.

One- and Two-Step Assay Methods

Assays of the invention are based on the covalent attachment of fluorophore-labeled collagen to a cell culture surface of a cell culture vessel. Cells are seeded onto the covalently-bound collagen and cultured in a culture medium appropriate for the particular cell type used. Depending on the cell type, culture condition, or presence of a test compound, the cells may or may not degrade the covalently-bound collagen. If degradation of the covalently-bound collagen occurs, fluorophore-labeled collagen fragments are released into the culture medium. The intensity of the fluorescence signal in a sample of the culture medium will reflect the concentration of fluorophore-labeled collagen fragments in the sample and, therefore, will reflect the amount of collagen degradation. A fluorescence signal can be detected either in the cell culture vessel itself (a "one-step assay") or after transfer of a sample of the cell culture medium to an assay vessel (a "two-step assay").

In some embodiments, osteoclasts or osteoclast precursors (as defined below) are seeded onto fluorophore-labeled collagen, preferably type I collagen, which is covalently bound to a culture surface of a cell culture vessel. If osteoclast precursors are used, the precursors are allowed to differentiate into multinucleated osteoclasts before carrying out the assay. Resorptive activity of the osteoclasts, as reflected by the release of fluorophore-labeled collagen fragments, can be measured by sampling the cell culture medium after an appropriate period of cell culture. Such assays directly measure the release of matrix metalloproteinases into the resorption lacuna of the osteoclast (Delaisse et al., Microsc Res Tech. 61:504-13, 2003). Assays of the invention also can be used, e.g., to screen for potential modulators (potential inhibitors or potential activators) of osteoclast function. For such screens, a test compound is added to a culture of differentiated osteoclasts before carrying out the assay. Assays of the invention also can be used to screen for modulators of osteoclast differentiation; in this case, a test compound is added to a culture of osteoclast precursors but is removed before the assay is carried out.

In other embodiments, assays of the invention can be used to monitor the function and/or differentiation of chondroclasts, which degrade cartilage types II and X, or other collagen-degrading cells, such as macrophages. Test compounds can be tested for their effects on the function and/or differentiation of such cells.

In still other embodiments, assays of the invention can be used to monitor collagen degrading activity of tumor cells (e.g., primary tumor cells, metastatic tumor cells, or cells of a metastatic or non-metastatic tumor cell line). To screen for compounds that may modulate this function, such as potential inhibitors of tumor metastasis, tumor cells are seeded onto fluorophore-labeled collagen, preferably type IV collagen, which is covalently bound to a culture surface of a cell culture vessel.

Components for Use in One- and Two-Step Assays

Cell Culture Vessel

Any vessel appropriate for culturing cells can be used as the cell culture vessel, provided the culture surface of the vessel (i.e., that portion of the inner surface of the vessel onto which the cells are seeded) is a material to which collagen can be covalently attached. Such vessels include, for example, commercially available tissue culture flasks or 1-, 4-, 6-, 8-, 12-, 24-, 96-, or 384-well plastic tissue culture plates or Petri dishes. Cell culture vessels can be made from any material which is appropriate for culturing cells and which can be derivatized to bind collagen covalently. Such materials include, but are not limited to, glass, polystyrene, polypropylene, polycarbonate, copolymers (e.g., ethylene vinylacetate copolymers), polyester, and the like.

Collagen

Any form of recombinant or naturally occurring collagen can be used in assays of the invention. The collagen is preferably vertebrate collagen, more preferably mammalian collagen, and even more preferably human collagen. The collagen is sufficiently intact and undenatured to permit its covalent binding to a culture surface of a cell culture vessel and to permit its degradation by enzymes released by cells cultured on the collagen. Preferably, the collagen is as intact and undenatured as possible, so as to increase specificity and sensitivity of assays of the invention.

Depending upon the cultured cell type, any type of collagen can be used (e.g., collagen types I, II, III, IV, V, VI, VII, VIII, VIX, or X, etc.). When osteoclasts or osteoclast precursors are used in an assay, type I collagen is preferred. Sources of type I collagen include rat tail collagen, bovine dermis collagen, human placental collagen, and kangaroo tail collagen. When tumor cells are used in an assay, type IV collagen is preferred. Sources of type IV collagen include human or other mammalian placental collagen and Engelbreth-Holm-Swarm mouse sarcoma collagen.

The collagen preparation preferably is as pure as possible so that detected fluorescence reflects true collagen degradation and not degradation of impurities. Collagen preparations that are at least about 90% pure (i.e., at least about 90% by weight of the protein in the preparation is collagen) are preferred; even more preferred are collagen preparations that are at least about 91, 92, 93, 94, 95, 96, 97, 98, or 99% pure. Preferably, the collagen is about 100% pure. "About" as used herein means "plus or minus 5% or less."

Fluorophore

Any fluorophore which can be covalently bound to collagen and still retain detectability can be used in assays of the invention. A large variety of such fluorophores are available including, but are not limited to, Alexa Fluor 350, Alexa Fluor 488, Alexa Fluor 546, Alexa Fluor 555, Alexa Fluor 594, Alexa Fluor 647, Alexa Fluor 680, fluorescein isothiocyanate (FITC), Rhodamine 110, Rhodamine 123, Rhodamine 6G, Rhodamine Green, Rhodamine Red, and Rhodamine B.

Other suitable fluorophores include quantum dots, i.e., semiconductor nanocrystals with size-dependent optical and electronic properties. Quantum dots demonstrate quantum confinement effects in their luminescent properties. When quantum dots are illuminated with a primary energy source, a secondary emission of energy occurs at a frequency that corresponds to the band gap of the semiconductor material used in the quantum dot. The band gap energy of a quantum dot varies with the diameter of the crystal. See U.S. Pat. No. 6,326,144.

Highly luminescent semiconductor quantum dots (zinc sulfide-capped cadmium selenide) have been covalently coupled to biomolecules for use in ultrasensitive biological detection. U.S. Pat. No. 6,656,695; Stupp et al., Science 277, 1242-48, 1977; Chan et al., Science 281, 2016-68, 1998. Compared with conventional fluorophores, quantum dot nanocrystals have a narrow, tunable, symmetric emission spectrum and are photochemically stable. Bonadeo et al., *Science* 282, 1473-76, 1998. See also Jaiswal et al., *Nat. Biotechnol.* 21, 47-51, 2003; Watson et al., *Biotechniques* 34, 296-300, 2003; Wu et al., *Nat. Biotechnol.* 21, 41-46, 2003; Kaul et al., *Cell Res.* 13, 503-07, 2003.

Lanthanide Chelates

Preferred fluorophores are lanthanide chelates (e.g, β-diketone chelates of cerium, praseodymium, neodymium, promethium, samarium, europium, gadolinium, terbium, dysprosium, holmium, erbium, thulium, or ytterbium), which can be used with time-resolved fluorescence techniques. Lanthanide chelates have a long fluorescence decay time and a very large Stokes' shift. These properties permit measurement of fluorescence after subsidence of the background fluorescence. See Soini and Kojola, *Clin. Chem.* 29, 65, 1983; Hemmila et al., Anal. Biochem. 137, 335 1984; Lovgren et al., In: Collins & Hoh, eds., *Alternative Immunoassays*, Wiley, Chichester, U.K., p. 203, 1985; Hemmila, *Scand. J. Clin. Lab. Invest.* 48, 389, 1988; Mikola et al., *Bioconjugate Chem.* 6, 235, 1995; Peruski et al., *J. Immunol. Methods* 263, 35-41, 2002; U.S. Pat. No. 4,374,120; and U.S. Pat. No. 6,037,185. Suitable β-diketones are, for example, 2-naphthoyltrifluoroacetone (2-NTA), 1-naphthoyltrifluoroacetone (1-NTA), p-methoxybenzoyltrifluoroacetone (MO-BTA), p-fluorobenzoyltrifluoroacetone (F-BTA), benzoyltrifluoroacetone (BTA), furoyltrifluoroacetone (FTA), naphthoylfuroylmethane (NFM), dithenoylmethane (DTM), and dibenzoylmethane (DBM). A preferred lanthanide chelate is $Eu^{3+}$-$N^1$-(p-isothiocyanatobenzyl) diethylenetriamine-$N^1$, $N^2$, $N^3$-tetraacetic acid (Perkin-Elmer). Lanthanide chelates are particularly well-suited for use in two-step assays.

Methods of Covalently Attaching a Fluorophore to Collagen

There are a variety of methods known in the art which are useful for covalently attaching a fluorophore to collagen. For example, the attachment can be direct via a functional group on the collagen (e.g., amino, carboxyl and sulfhydryl groups) and a reactive group on the fluorophore. Free amino groups in the collagen can be reacted with fluorophores derivatized with isothiocyanate, maleic anhydride, N-hydroxysuccinimide, tetrafluorylphenyl and pentafluoryl esters. Free carboxyl groups in the collagen can be reacted with carbodiimides such as 1-ethyl-3-[dimethylaminopropyl]carbodiimide hydrochloride to create a reactive moiety that will react with an amine moiety on the fluorophore. Collagen sulfhydryl groups can be attached to fluorophores modified with maleimide and iodoacetyl groups, although such linkages are more susceptible to reduction than linkages involving free amino groups. The collagen can also be linked indirectly via an intermediate linker or spacer group, using chemical groups such as those listed above. Collagen can be attached by any stable physical or chemical association to a hydrophilic attachment group of a water-soluble quantum dot directly or indirectly by any suitable means, such as those described in U.S. Pat. No. 6,468,808 and U.S. Pat. No. 6,236,144.

Covalent Attachment of Fluorophore-Labeled Collagen to a Cell Culture Vessel

Fluorophore-labeled collagen can be covalently attached to a derivatized surface of a cell culture vessel using any method known in the art. For example, the attachment can be direct via a reactive group on the collagen (e.g.; amino, carboxyl and sulfhydryl groups) and a chemical entity on the plastic surface. Free amino groups can be reacted with maleic anhydride, N-hydroxysuccinimide, tetrafluorylphenyl and pentafluoryl esters, free carboxyl groups can be reacted with carbodiimides such as 1-ethyl-3-[dimethylaminopropyl]carbodiimide hydrochloride to create a reactive moiety that can be attached to an amino-modified plastic surface, and collagen sulfhydryl groups can be attached to a plastic surface modified with maleimide and iodoacetyl groups. The collagen can also be linked indirectly via an intermediate linker or spacer group, using chemical groups such as those listed above.

A soluble fluorescein-labeled collagen is commercially available from Molecular Probes, Inc. ("DQ collagen") and can be used in one-step assays of the invention. The fluorescein-labeled collagen is so heavily labeled that internal quenching of the fluorophore occurs; thus, the fluorescein label can be detected only when degradation separates some of the fluorescein moieties sufficiently to avoid quenching. Other fluorophores can also be used to heavily label collagen and cause internal quenching.

If DQ collagen (or other similar heavily labeled collagen) is used, it is preferably not attached to a cell culture vessel using free amino groups; such attachment vastly reduces the sensitivity of two-step assays of the invention, probably because the heavy fluorescein labeling renders the majority of DQ collagen's free amino groups unavailable for binding to the cell culture surface of a cell culture vessel. See Example 13. It is preferred that DQ collagen be attached to a cell culture vessel by other means (e.g., via stable thioether linkages or via carboxyl groups).

Cells and Culture Conditions

Assays of the invention can be used with any type of cell which either can degrade collagen or that can differentiate into a cell which can degrade collagen. For example, cells such as osteoclasts, osteoclast precursors, or tumor cells can be used. "Osteoclasts" as used herein includes differentiated osteoclasts as well as osteoclast-like cell lines. "Osteoclast precursors" as used herein includes pre-osteoclasts, osteoclast progenitors, and osteoclast precursor cell lines. "Tumor cells" as used herein includes primary tumor cells, metastatic tumor cells, or tumor cell lines (either metastatic or non-metastatic). Purified cell populations (i.e., populations in which all or a majority of the cells are the desired type of cell) need not be used.

Osteoclasts or osteoclast precursors can be, for example, avian or mammalian. Avian osteoclasts or osteoclast precursors are disclosed, for example, in Collin-Osdoby et al., Methods Mol Med. 2003; 80:65-88; Collin-Osdoby et al., J Bone Miner Res. 2002 October; 17(10):1859-71. Suitable mammalian osteoclasts or osteoclast precursors include, but are not limited to, those of rodents, such as rat (Bushinsky, J Bone Miner Res. 1994 November; 9(11):1839-44) or mouse (Takahashi et al., Methods Mol Med. 2003; 80:129-44); rabbit (Coxon et al., Methods Mol Med. 2003; 80:89-99; Shimizu et al., Bone Miner. 1989 July; 6(3):261-75); non-human primates (Povolny & Lee, Exp Hematol. 1993 April; 21(4):532-7; Takahashi et al., J Bone Miner Res. 1987 August; 2(4):311-7); and humans (Sabokbar & Athanasou, Methods Mol Med. 2003; 80:101-11; Benito et al., Cytometry. 2002 Oct. 15; 50(5):261-6).

A preferred source of human osteoclast precursors are those available from Cambrex Corporation ("Poietics™ Osteoclast Precursors," product no. 2T-110). See Example 2 for a description of preferred culture conditions for these cells. Culture medium and additives for culturing osteoclast precursor cells can also be obtained from Cambrex Corporation (e.g, PT-8001; PT-8201; PT-9501).

Other suitable cells include, but are not limited to, MOCP-5 osteoclast precursors (Chen & Li, J Bone Miner Res. 1998 July; 13(7):1112-23); osteoclast-inductive and osteoclastogenic cell lines from the H-2 $K^b$tsA58 transgenic mouse (Chambers et al., *Proc. Natl. Acad. Sci. USA* 90, 5578-

82, 1993); and the immortalized osteoclast (OCL) precursor cell line derived from mice doubly transgenic for bcl-XL and large T antigen (Hentunen et al., *Endocrinology* 140, 2954-61, 1999). Pre-osteoclast and osteoclast-like cell lines also can be used. See, for example, Fiorelli et al., *Proc. Natl. Acad. Sci. USA* 92, 2672-76, 1995; Miyamoto & Suda, Keio *J. Med.* 52, 1-7, 2003; Arai et al., *J. Exp. Med.* 190, 1741-54, 1999; Espinosa et al., *J. Cell Sci.* 115, 3837-48, 2002; Mbalaviele et al., *J. Cell Biol.* 141, 1467-76, 1998; Thomas et al., *Endocrinol.* 140, 4451-58, 1999; Quinn et al., *Endocrinol.* 139, 4424-27, 1998; Itoh et al., *Endocrinol.* 142, 3656-62, 2001; and Ragab et al., *Am. J. Physiol. Cell Physiol.* 283, C679-C687, 2002. See also MacDonald et al., *J Bone Miner Res.* 1986 April; 1(2):227-33.

Primary tumor cells typically are mammalian cells, such as rat, mouse, guinea pig, rabbit, non-human primate, or human cells. They can be obtained, for example, from spontaneously arising tumors in non-human mammals or in humans (e.g., from surgical or biopsy samples) or from tumors seeded in an experimental non-human mammalian model. Such tumors include, but are not limited to, melanomas, non-small cell lung tumors, small cell lung tumors, renal tumors, colorectal tumors, breast tumors, pancreatic tumors, gastric tumors, bladder tumors, ovarian tumors, uterine tumors, lymphoma cells, leukemia cells, and prostate tumors. Metastatic tumor cells can be obtained, for example, from metastases of primary tumors.

Alternatively, mammalian, preferably human, metastatic or non-metastatic cell lines can be used. Metastatic cell lines include, e.g., melanoma cell lines A2058, Mv3, BLM, SK-MEL-19, Hs 688(A).T, WM-115, and 1F6m; breast cancer cell lines MDA 435, MDA 231, and Hs578T; rhabdomyosarcoma cell line SMF-Ai; prostate tumor cell line DU145/M, PC-3-M; colorectal adenocarcinoma cell line SW480; gastric adenocarcinoma cell line RF-1; lung squamous cell carcinoma cell line KLN 205; and osteosarcoma cell line KHOS. Non-metastatic cell lines include rhabdomyosarcoma cell line SMF-Deposit Account No. 19-0733, breast cancer cell lines NM-2C5, MDA-MB-231, or MCF-7, melanoma cell line 530, and prostate cancer cell line LNCaP.

The selection of an appropriate culture medium for a given cell type, as well as other culture conditions such as temperature and percent $CO_2$, is well within the skill of those in the art (see, for example, ANIMAL CELL CULTURE, R. I. Freshney, ed., 1986).

Culture times can be varied according to the type of cells cultured. For example, if osteoclast precursors are used, they typically are cultured at least 3-4 days before an assay is carried out so that the cells can differentiate into functional osteoclasts (see FIG. 1). If osteoclasts or osteoclast-like cell lines are used, assays can be carried out almost immediately after seeding.

Assay Vessel for Use in Two-Step Assays of the Invention

The assay vessel can be a plastic or glass plate and can be clear, white, or preferably black. More preferably, an assay vessel is black-walled with a clear bottom surface. The assay vessel can have multiple wells (e.g., 96 or 384 wells) to facilitate high throughput assays.

Detection of Fluorescence Signal

Detection of the fluorescence signal in either a one-step or a two-step assay of the invention can be either qualitative or quantitative. Fluorophore-labeled collagen fragments can be detected by methods known in the art for detecting the particular fluorophore used. For example, if the collagen is labeled with fluorescein, its fluorescence can be detected by use of a fluorimeter with excitation and emission wavelengths of 485 and 535 nm, respectively. Other fluorophores will have their own unique excitation and emission maxima, and these are known in the art. Some types of fluorophores, such as quantum dots, can be imaged by use of image analysis systems that detect fluorescence.

Detection of Time-Resolved Fluorescence of Lanthanide Chelates

Lanthanide chelates are typically used in two-step assays of the invention. If desired, fluorescence associated with a lanthanide chelate can be measured without dissociating the lanthanide ion from the chelate (see U.S. Pat. No. 4,808,541). Preferably, however, a low pH enhancement solution is used to dissociate the lanthanide label from the labeled collagen; free lanthanide (e.g., $Eu^{3+}$, $Sm^{3+}$, $Tb^{3+}$, $Dy^{3+}$) then forms a stable, fluorescent chelate with components of the enhancement solution within a protective micelle.

The enhancement solution can contain a suitable detergent, such as Triton X-100, and a β-diketone to amplify the fluorescence after the separation. To further improve the fluorescence, especially in aqueous solutions, a synergistic compound such as a Lewis base can be added. Suitable synergistic compounds include N-heterocyclic compounds (e.g., o-phenanthroline), as well as phosphines and phosphine oxides (e.g. trioctylphosphineoxide) (see U.S. Pat. No. 4,565, 790). The EG&G Wallac DELFIA® method is particularly useful for measuring fluorescence associated with a lanthanide chelate. See, e.g., U.S. Pat. Nos. 5,998,146; 5,859, 215; 5,637,509; and 5,457,186.

One suitable enhancement solution comprises 15 PM β-naphthoyltrifluoroacetone, 50 µM trioctylphosphine oxide, 0.1% Triton X-100 in phthalatacetate buffer, pH 3.2 (see U.S. Pat. No. 4,808,541, incorporated herein by reference). DELFIA® Enhancement Solution (EG&G Wallac) is preferred, but any acidic solution sufficient to cause the lanthanide ion to dissociate from the chelating agent and complex with a second chelating agent, such as a β-diketone, to form a fluorescent chelate can be used.

Fluorescence preferably is detected by a method using time delay, which reduces or eliminates the contribution of non-specific background fluorescence to the detected signal. A preferred method of detection is time-resolved fluorometry, which is especially well suited for use with fluorescent lanthanide chelates (Soini et al., *Clin. Chem.* 25, 353-61, 1979; U.S. Pat. No. 4,374,120; see also Example 1, below). Devices suitable for carrying out time-resolved fluorimetry include a Victor spectrofluorimeter (e.g., Victor or Victor²™ from EG&G Wallac), SPECTRAmax GEMINI (Molecular Devices), the LJL-Analyst, and FLUOstar from BMG Lab Technologies. See also U.S. Pat. No. 6,042,785.

Test Compounds

Test compounds to be screened for an ability to modulate collagen degradation, especially for an ability to inhibit collagen degradation, can be any pharmacologic agents already known in the art or can be compounds previously unknown to have any pharmacological activity. Test substances can be naturally occurring or synthesized in the laboratory. They can be isolated from microorganisms, animals, or plants, or can be produced recombinantly or synthesized by chemical methods known in the art.

Test compounds also can be obtained from compound libraries. Methods of generating combinatorial libraries of test compounds are known in the art and include, but are not limited to, formation of "biological libraries," spatially addressable parallel solid phase or solution phase libraries, synthetic library methods requiring deconvolution, the "one-bead one-compound" library method, and synthetic library methods using affinity chromatography selection. See, e.g., DeWitt et al., *Proc. Natl. Acad. Sci. U.S.A.* 90, 6909, 1993; Erb et al., *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061, 1994; Gallop et al., *J. Med. Chem.* 37, 1233, 1994; and Lam, *Anticancer Drug Des.* 12, 145, 1997.

Test compounds can be presented to cells, for example, in solution (Houghten, *Biotechniques* 13, 412-21, 1992), on beads (Lam, *Nature* 354, 82-84, 1991), in plasmids (Cull et al., *Proc. Natl. Acad. Sci. U.S.A.* 89, 1865-69, 1992), or in phage (Scott & Smith, *Science* 249, 386-90, 1990; Devlin, *Science* 249, 404-06, 1990; Cwirla et al., *Proc. Natl. Acad. Sci.* 97, 6378-82, 1990; Felici, *J. Mol. Biol.* 222, 301-10, 1991; and U.S. Pat. No. 5,223,409).

Cell Culture Vessels

The invention also provides cell culture vessels for use in performing assays of the invention. Cell culture vessels of the invention are those vessels described above to which fluorophore-labeled collagen is covalently attached. The physical form of the cell culture vessel is relatively unimportant as long as the vessel permits covalent attachment of fluorophore-labeled collagen and satisfactory culture of collagen-degrading cells.

Preferred cell culture vessels contain covalently attached europium chelate-labeled collagen, e.g., collagen labeled with $Eu^{3+}$-N'-(p-isothiocyanatobenzyl) diethylene-triamine-$N^1,N^2,N^3$-tetraacetic acid. More preferred cell culture vessels are maleic anhydride-derivatized polystyrene tissue culture plates to which europium chelate-labeled human type I collagen or europium chelate-labeled type IV collagen is covalently bound. Other preferred cell culture vessels contain covalently bound fluorophore-labeled collagen that is internally quenched and does not fluoresce (such as DQ collagen).

Kits

The invention also provides kits for carrying out assays of the invention. The kits can comprise, for example, one or more cell culture vessels of the invention and instructions for carrying out one or more embodiments of the assays disclosed herein. The kits can contain other components, such as assay vessels, reagents for detecting fluorescence (e.g., an enhancement solution), buffers, osteoclasts or osteoclast precursors, tumor cells, culture medium growth factors, and fluorescence standards (e.g., a europium standard).

In a preferred embodiment, a kit comprises an enhancement solution, a maleic anhydride-derivatized polystyrene tissue culture plate to which europium chelate-labeled human type I collagen is covalently bound, and instructions for carrying out an OsteoLyse™ assay. In another preferred embodiment, a kit comprises an enhancement solution, a maleic anhydride-derivatized polystyrene tissue culture plate to which europium chelate-labeled type IV collagen is covalently bound, and instructions for carrying out an assay to detect collagen degradation activity by tumor cells. The preferred europium chelate for use in such kits is $Eu^{3+}$-$N^1$-(p-isothiocyanatobenzyl) diethylenetriamine-$N^1,N^2,N^3$-tetraacetic acid. Other kits comprise a cell culture vessel to which a fluorophore-labeled collagen is covalently attached and instructions for carrying out a one-step assay, a two-step assay, or both types of assay. In some kits, fluorescence of the fluorophore-labeled collagen is internally quenched.

All patents, patent applications, and references cited in this disclosure are expressly incorporated herein by reference in their entireties. The above disclosure generally describes the present invention. A more complete understanding can be obtained by reference to the following specific examples, which are provided for purposes of illustration only and are not intended to limit the scope of the invention.

EXAMPLE 1

OsteoLyse™ Assay Protocol

This example describes steps in one embodiment of a two-step assay of the invention, termed an "OsteoLyse™ assay."

Remove a 96-well cell culture plate to which europium chelate-labeled collagen (e.g., collagen labeled with $Eu^{3+}$-N'-(p-isothiocyanatobenzyl) diethylenetriamine-$N^1,N^2,N^3$-tetraacetic acid) is covalently bound from 4° C. storage and let it warm to room temperature. Seed mature osteoclasts or osteoclast precursors (human or non-human) onto the cell culture plate in medium containing M-CSF and soluble RANK ligand. If using Cambrex's primary human osteoclast precursors (Poietics™ Human Osteoclast Precursors), seed the cells at a density of 10,000 cells/well in osteoclast precursor differentiation medium (Cambrex product # PT-8001). See Example 2 for a detailed protocol for the culture of primary human osteoclast precursors (Cambrex product # 2T-110). Precursors cultured in the absence of soluble RANK ligand can serve as "undifferentiated" controls.

Culture the cells for 6 days and then renew the cell culture medium. Fresh medium preferably contains the same concentrations of M-CSF and soluble RANK ligand as in the original day 0 medium. Unused control and differentiation media from day 0 can be frozen (on day 0) and used for the day 6 medium changes.

At least two different types of protocols can be used. If the assay is used to measure the effect of a test compound on differentiation of the osteoclast precursor, the test compound typically is added at day 0 and removed at day 6. However, if the assay is used to measure the effect of a test compound on mature osteoclast function (i.e., bone matrix collagen degradation), the test compound typically is added at day 6 with the new medium addition.

The cell culture medium can be sampled at any time after the medium change. Because a very small volume (5 to 10 µl) of medium is sampled, it is very easy to do time-course studies by repeatedly sampling the medium on sequential days. Medium volumes greater than 10 µl are unnecessary and, because an excess of fluorophore releasing reagent with respect to sample is desired, actually may lead to inefficient counting of the fluorophore as the ratio of fluorophore releasing reagent to sample decreases.

Prior to sampling the cell culture medium, remove the fluorophore releasing reagent (DELFIA® Enhancement Solution, available as "Fluorophore Releasing Reagent" from Cambrex Corp.) from 4° C. storage and let it warm to room temperature—do not warm this reagent in a water bath. Place 200 µl of the fluorophore releasing reagent in each well of a black/black-wall 96-well assay vessel; black-walled low background plates are recommended.

Transfer 10 µl of cell culture medium to the wells of the assay vessel containing fluorophore releasing reagent using a separate pipette tip for each new cell culture medium. Briefly mix the samples in tie assay vessel.

Determine the fluorescence of each well of the assay vessel in a time-resolved fluorescence fluorimeter (e.g., a Wallac Victor, with excitation at 340 nm and emission at 615 µm) over a 400 second time period after an initial delay of 400 µseconds.

If the amount of collagen degraded as a percentage of the total available collagen is to be calculated, determine the total amount of intact collagen per well by placing 200 µl of fluorophore releasing reagent in each of three unused wells of the culture plate. Mix the contents of the wells and then transfer 1 µl per well to corresponding wells in an assay vessel containing 200 µl of fluorophore releasing reagent per well as described in paragraph [64], above. Determine the fluorescence of each well of the assay vessel in a time-resolved fluorescence fluorimeter and multiply the result by 200 to calculate the total amount of intact collagen per well.

EXAMPLE 2

Culture of Human Osteoclast Precursors

This example provides detailed instructions for culturing Poietics™ Human Osteoclast Precursors for either one- or two-step assays of the invention.

Preparation of Media

Use pre-warmed (37° C.) supplemented medium for culturing osteoclast precursors. Decontaminate the external surfaces of a 100 ml bottle of Osteoclast Precursor Basal Medium (Cambrex product no. PT-8201) with 70% v/v ethanol or isopropanol. Make up Osteoclast Precursor Growth Medium by adding fetal bovine serum (FBS), L-glutamine, penicillin and streptomycin "SingleQuots" to the bottle of Osteoclast Precursor Basal Medium; the final concentrations of the supplements will be 10%, 2 mM, 100 units/ml and 100 µg/ml respectively.

Thawing of Cells/Initiation of Culture Process

Warm 100 ml of Osteoclast Precursor Growth Medium in a 37° C. water bath. Quickly but completely thaw the vial of frozen cells in a 37° C. water bath. Wipe the outside of the vial with 70% ethanol. Aseptically transfer the cell suspension to a 50 ml conical tube. Rinse the cryovial with 1 ml of Osteoclast Precursor Growth Medium. Add the rinse dropwise to the cells while gently swirling the tube (=1 minute).

Slowly add additional medium drop-wise to the cells until the total volume is 5 ml, while gently swirling after each addition of several drops of medium (~3 minutes). Slowly bring the volume up to 40 ml by adding 1 to 2 ml volumes of medium drop wise, while gently swirling after each addition of medium (~10 minutes).

Centrifuge the cell suspension at 200×g at room temperature for 15 minutes. Carefully remove by pipette and save most of the wash, leaving approximately 3 ml behind so the cell pellet is not disturbed. Gently resuspend the cell pellet in the remaining medium and transfer to a 15 ml conical tube.

Rinse the 50 ml conical tube with 2 ml of Osteoclast Precursor Growth Medium and add drop-wise to the cells in the 15 ml conical tube. Slowly bring the volume up to 10 ml by adding 1 to 2 ml volumes of Osteoclast Precursor Growth Medium drop-wise while gently swirling after each addition of medium.

Centrifuge the cell suspension at 200×g at room temperature for 15 minutes. Carefully remove by pipette all but 1 ml of the wash. Gently resuspend the cell pellet in the remaining medium and count (e.g, using a hemocytometer). When washing the cells, do not attempt to remove too much of the wash. Leave a minimum of 1 ml of wash at the bottom of the tube. If the final cell count is low, some of the pellet may have been removed with the wash.

Dilute 20 µl of the cell suspension in 20 µl of 0.4% Trypan Blue and do a cell count and determine % viability. Recovery should be greater than 90%. If the cell count is lower than expected, centrifuge the previously saved wash at a higher speed, count, and combine if necessary.

Maintenance and Osteoclast Precursor Differentiation Procedure

Primary human osteoclast precursors cannot be "passaged." They can be differentiated, but in the absence of specific differentiation signals, the cells will senesce. As a negative control, some cells can be cultured in the absence of soluble RANK ligand. While the precursors will expand in number, no functional differentiated osteoclasts will develop in controls without soluble RANK ligand.

If the Precursors are not to be Treated with Test Samples

To prepare Osteoclast Differentiation Medium (Cambrex product no. PT-8201), add the entire contents of the M-CSF SingleQuot to 30 ml of Osteoclast Precursor Growth medium—the final concentration will be 33 ng/ml. The vial of M-CSF may have to be centrifuged at very low speed to recover the entire content of the vial. Remove 1 ml of the M-CSF supplemented medium for the culture of undifferentiated control cells.

Add 1.0 ml of the medium containing M-CSF to a vial of lyophilized soluble RANK ligand. Cap the vial, mix and remove the contents and add the RANK ligand SingleQuot to the remaining 29 ml of the M-CSF supplemented medium. The final concentration of soluble RANK ligand will be 66 ng/ml. Add osteoclast precursors to the control and Differentiation Medium at a concentration of 50,000 cells/ml. Seed 10,000 osteoclast precursors/well at 0.2 ml/well.

If the Precursors are to be Treated with Test Samples

To prepare Osteoclast Differentiation Medium, add the entire contents of the M-CSF SingleQuot to 15 ml of Osteoclast Precursor Growth medium—the final concentration will be 33 ng/ml upon addition of 0.1 ml of test sample. The vial of M-CSF may have to be centrifuged at very low speed to recover the entire content of the vial. Remove 0.5 ml of M-CSF supplemented medium for the culture of undifferentiated control cells.

Add 1.0 ml of the medium containing M-CSF to the vial of lyophilized soluble RANK ligand. Cap the vial, mix and remove the contents and add the RANK ligand SingleQuot to the remaining 14.5 ml of the M-CSF supplemented medium. The final concentration of soluble RANK ligand will be 66 ng/ml upon addition of 0.1 ml of test sample.

Add osteoclast precursors to the control and Differentiation Medium at a concentration of 100,000 cells/ml. Seed 10,000 Osteoclast Precursors/well at 0.1 ml/well.

Set up a 24-well dilution plate with appropriate volumes of Osteoclast Precursor Growth Medium/well and make serial dilutions of the test sample(s) to be assayed. Add 0.1 ml of each different concentration of test sample to the wells of osteoclast precursors. Each assay should be done in triplicate.

Control wells can be set up which contain 1) no added test sample and 2) solvent only if the test samples were dissolved in solvents such as DMSO, ethanol, etc.

Cell Culture

Incubate the cells at 37° C. in a humidified atmosphere of 5% $CO_2$.

Day 7 osteoclasts can be identified by phase microscopy as unusually large multinucleate cells. The majority of each well's bottom surface should be covered by such cells. The culture can be continued for an additional week, with or without feeding, during which time the osteoclasts will continue to increase in size.

To document osteoclast differentiation, cultures can be stained for the $\alpha_v\beta_3$ integrin complex or for tartrate-resistant acid phosphatase (TRAP).

EXAMPLE 3

Release of Fluorescent Collagen Peptides Over Time in an OsteoLyse™ Assay

Primary human osteoclast precursors were seeded onto europium chelate-labeled collagen ($Eu^{3+}$-N'-(p-isothiocyanatobenzyl) diethylenetriamine-$N^1,N^2,N^3$-tetraacetic acid; Perkin-Elmer) covalently bound to a maleic anhydride-derivatized polystyrene plate (Pierce Reacti-Bind™) at 10,000 cells/well and cultured in medium containing M-CSF and soluble RANK ligand as described in Example 2. Samples of culture medium (10 µl) were removed every 24 hours and counted in 200 µl Fluorophore Releasing Reagent (DELFIA® Enhancement Solution) in a time-resolved fluorescence-capable plate reader.

The release of fluorescent collagen peptides by differentiating primary human osteoclasts occurs between the third and fourth days of culture. See FIG. 1.

Figure 2:
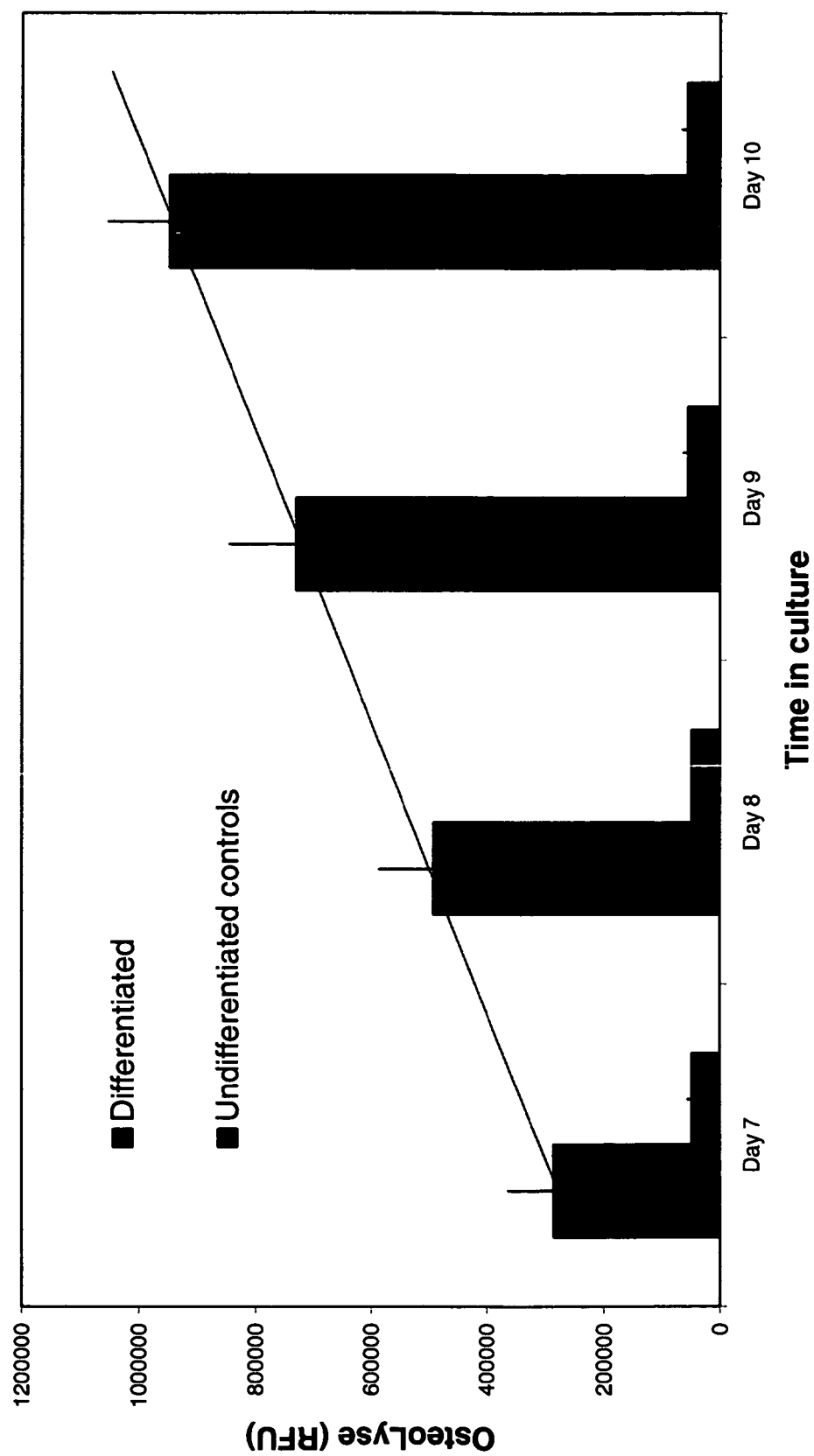
FIG. 2. Graph showing the release over time of europium chelate-labeled degradation fragments of collagen on days 7, 8, 9, and 10 from an OsteoLyse™ plate on which osteoclast precursors were cultured.

The fluorescence of the medium samples diluted in the wells with Fluorophore Releasing Reagent is directly proportional to the resorptive activity of the mature osteoclast. The fluorescent read-out of the OsteoLyse™ assay is proportional to cell number and the degree of osteoclast differentiation. See FIG. 2 for documentation that the accumulation of collagen fragments is directly related to duration of cell culture.

The release of collagen degradation fragments was substantially linear with time and the signal-to-background ratio, which also increased with time, was as high as 38 after 10 days of culture. The coefficient of variation of the OsteoLyse™ assay was <20% and the Z' value ranged from 0.5 to 0.7.

EXAMPLE 4

Release of Fluorescent Collagen Peptides after a Change of Medium in an OsteoLyse™ Assay Primary human osteoclast precursors were seeded onto europium chelate-labeled collagen covalently bound to a maleic anhydride-derivatized polystyrene plate (Pierce Reacti-Bind™) at 10,000 cells/well and cultured in medium containing soluble RANK ligand. The medium was changed after day 6.

Samples of culture medium (10 µl) were removed and counted in 200 µl Fluorophore Releasing Reagent (DELFIA® Enhancement Solution) in a time-resolved fluorescence-capable plate-reader, after 7, 8, 9 and 10 days of total cell culture time.

Figure 3:
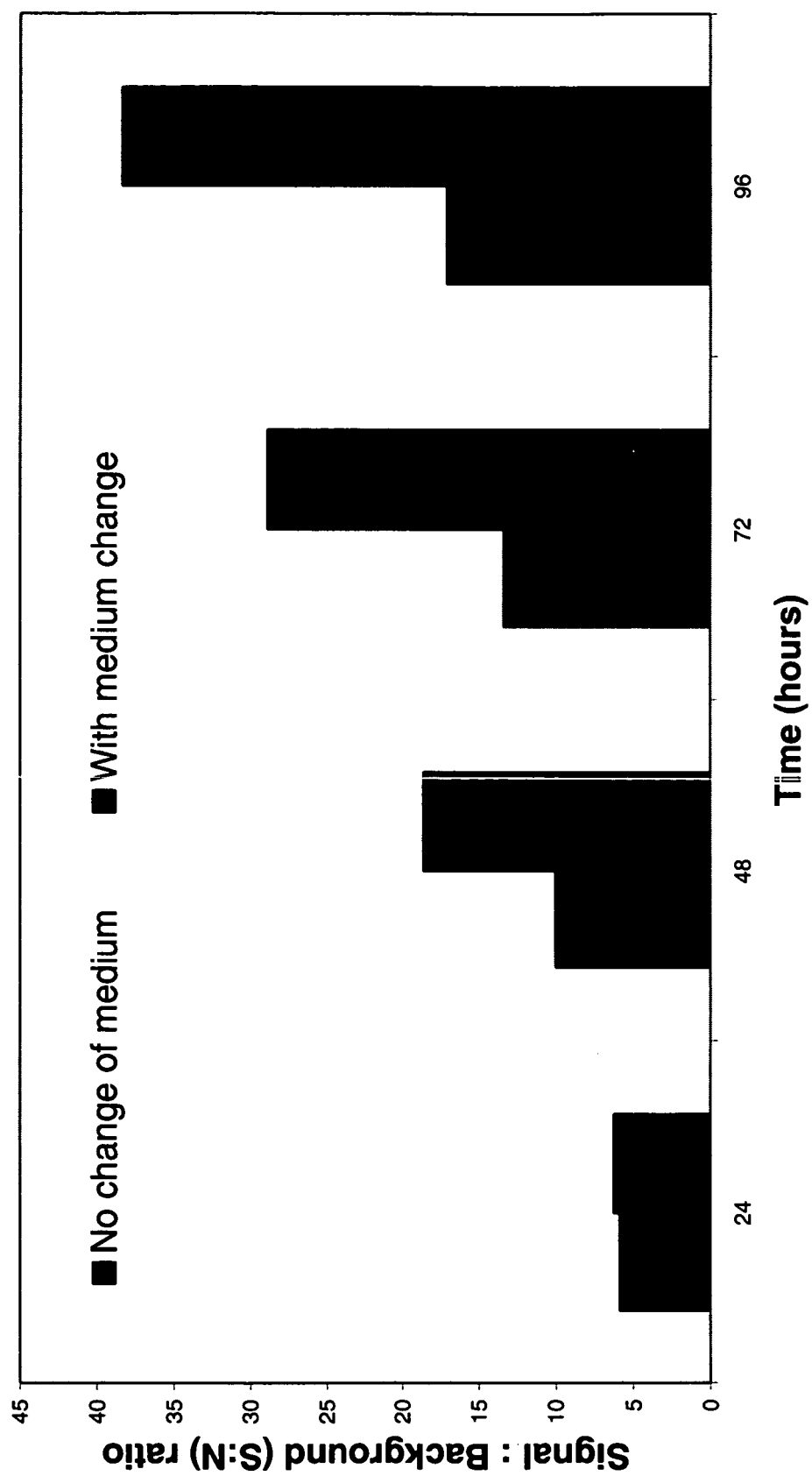
FIG. 3. Graph showing increase of signal-to-noise ratio over time in an OsteoLyse™ assay with and without a change in medium.

The signal-to-noise (S:N) ratios of the OsteoLyse™ assay increases with time of incubation and after a day 6 change of medium. These results are shown in FIG. 3. Left bar of each pair of bars=no change of medium; right bar of each pair of bars=with medium change.

EXAMPLE 5

Figure 4A:
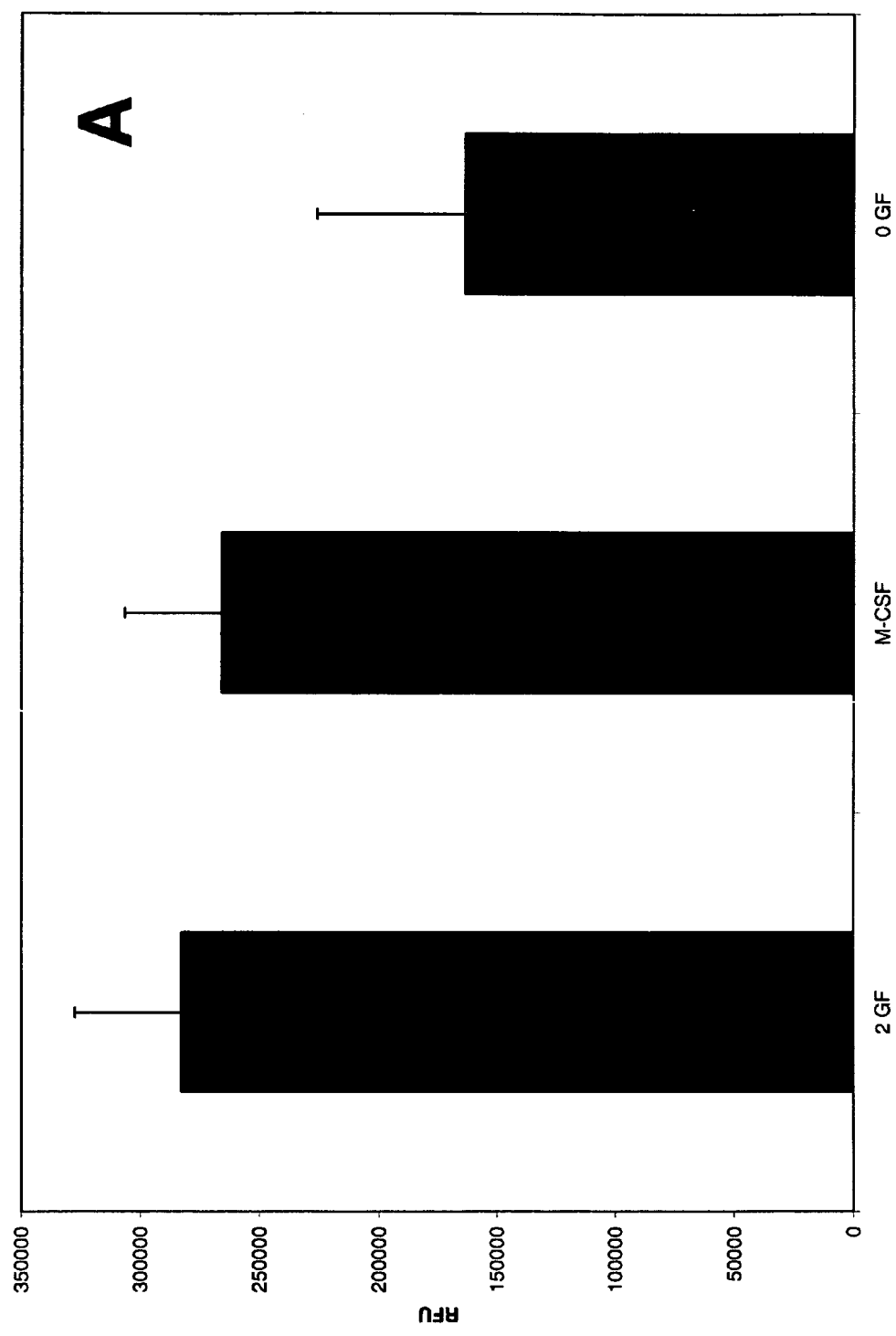
FIG. 4A plots results after one additional day in culture.
Figure 4B:
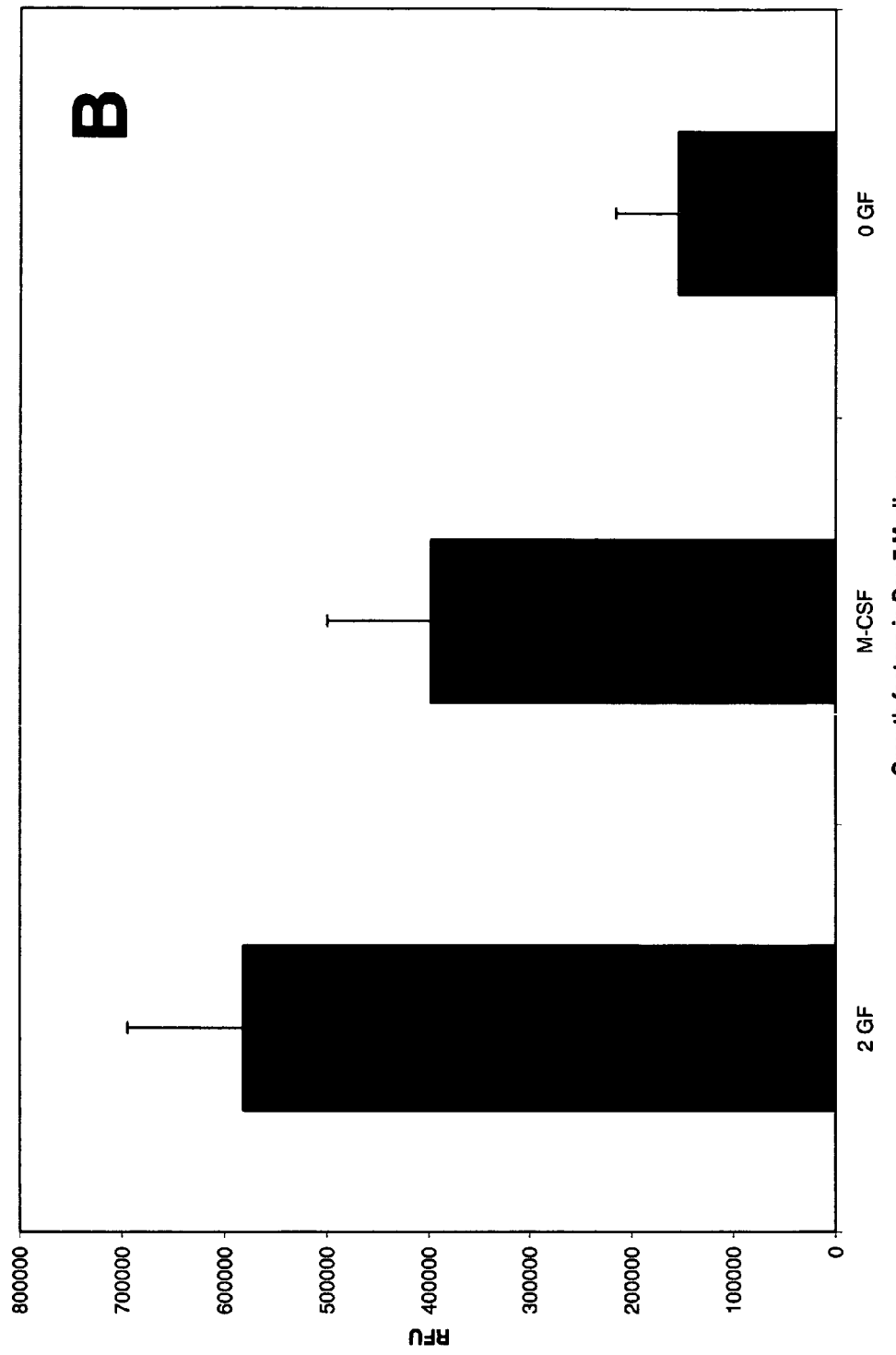
FIG. 4B plots results after two additional days in culture.
Figure 4C:
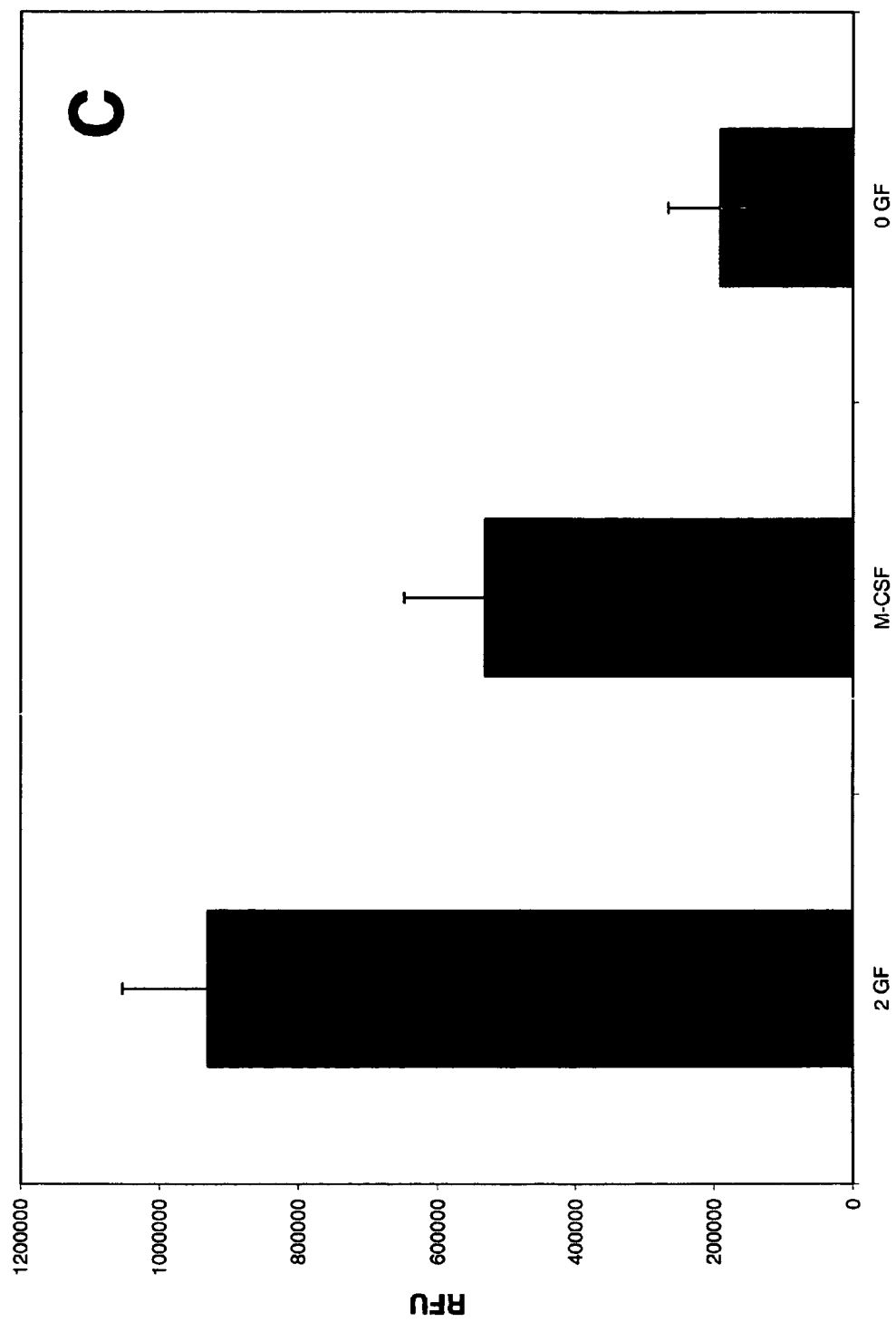
FIG. 4C plots results after three additional days in culture.

Dependence of Osteoclast Collagen-Degrading Activity on M-CSF and Soluble RANK Ligand in an OsteoLyse™ Assay Primary human osteoclast precursors were seeded onto europium chelate-labeled collagen covalently bound to a maleic anhydride-derivatized polystyrene plate (Pierce Reacti-Bind™) at 10,000 cells/well and cultured in differentiation medium. After 7 days of culture, the medium with and without various combinations of M-CSF and soluble RANK ligand, was renewed. Samples of culture medium (10 µl) were removed and counted after an additional 1 (FIG. 4A), 2 (FIG. 4B) and 3 (FIG. 4C) days. "2 GF"=M-CSF (33 ng/ml) and RANK ligand (66 ng/ml); "0 GF"=neither M-CSF nor RANK ligand.

This example demonstrates that the collagen-degrading activity of differentiated (day 6) primary human osteoclasts is dependent upon the presence of both M-CSF and soluble RANK ligand.

EXAMPLE 6

Inhibition of Bone Matrix Resorption by Calcitonin in an OsteoLyse™ Assay

Primary human osteoclast precursors were seeded onto europium chelate-labeled collagen covalently bound to a maleic anhydride-derivatized polystyrene plate (Pierce Reacti-Bind™) at 10,000 cells/well and cultured in differentiation medium containing (1) no calcitonin, (2) calcitonin added only at day 5, or (3) calcitonin added on both days 0 and 5. Ten µl samples of culture media were counted after a total of 6 days. Measurement of the in vitro inhibition of bone resorption by alendronate was also assayed similarly in an OsteoLyse™ assay and gave an $IC_{50}$ value of approximately 2 µM.

Figure 5:
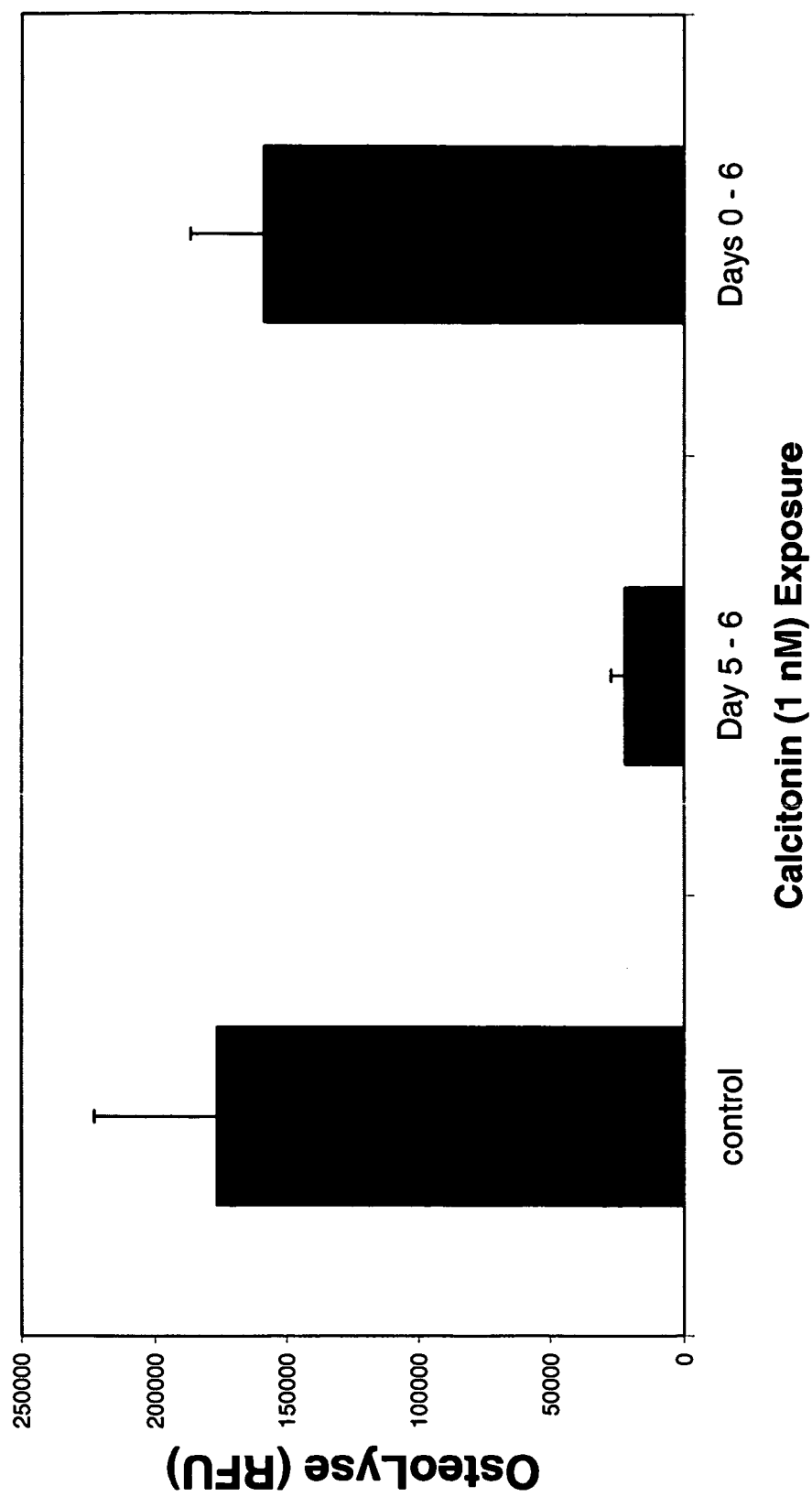
FIG. 5. Graph showing effects of calcitonin on osteoclast-mediated bone matrix degradation in vitro.

The results are shown in FIG. 5. Treatment of human osteoclasts with 1 mM calcitonin for 24 hours (day 5 of culture) inhibited bone matrix degradation by 88%. Treatment of the cells with calcitonin after prior exposure to calcitonin on day 0 had little effect on the resorptive activity of the osteoclasts. Calcitonin added at day 0 effectively resulted in the osteoclasts becoming refractory to calcitonin added on day 5.

EXAMPLE 7

Comparison of TRAP and OsteoLyse™ Assays

Primary human osteoclast precursors were seeded onto europium chelate-labeled collagen covalently bound to a maleic anhydride-derivatized polystyrene plate at 10,000 cells/well and cultured in medium containing soluble RANK ligand with and without interferon γ. After 9 days, cell culture media were assayed for fluorescent collagen peptides as described in Example 1. Cells in the plate were subsequently stained for TRAP (Sigma # 386-A).

Figure 6:
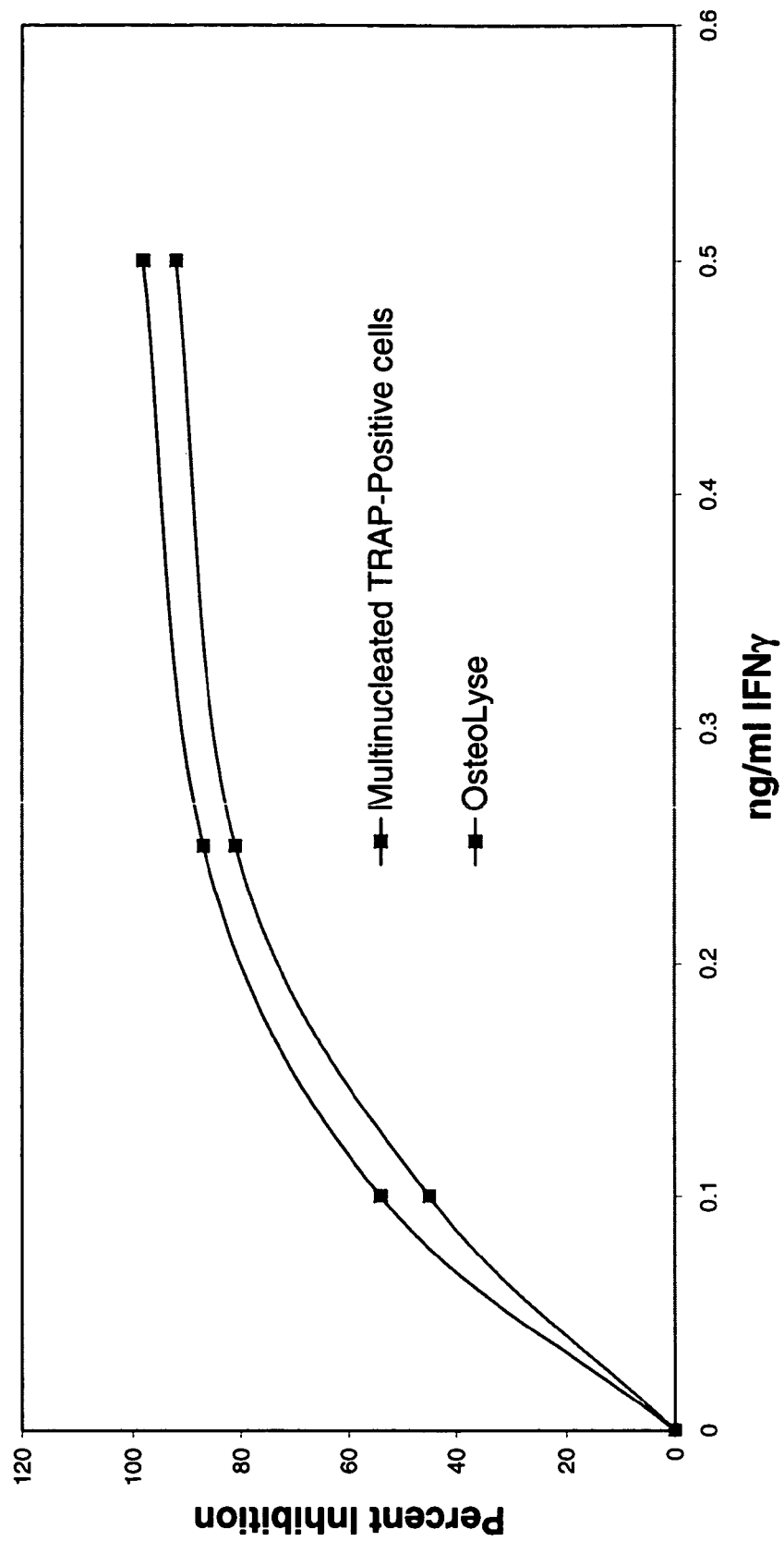
FIG. 6. Graph showing comparison of the TRAP Stain and an assay of the invention. The upper line denotes TRAP data (day 8 multinucleated TRAP-positive cells/well) while the lower line represents OsteoLyse™ assay data.

The results are shown in FIG. 6. Data are expressed as percent inhibition relative to controls not treated with interferon γ. Upper curve, results of TRAP assay. Lower curve, results of OsteoLyse™ assay. Data from these two assays gave nearly identical results with $IC_{50}$ values of approximately 0.1 ng/ml.

EXAMPLE 8

Comparison of TRAP and OsteoLyse™ Assays in Determinations of Alendronate-Mediated Inhibition of Osteoclast Function Primary human osteoclast precursors were seeded onto europium chelate-labeled collagen covalently bound to a maleic anhydride-derivatized polystyrene plate at 10,000 cells/well and cultured in medium containing M-CSF only or in medium containing both M-CSF and soluble RANK ligand with and without alendronate (10 µM).

Figure 7:
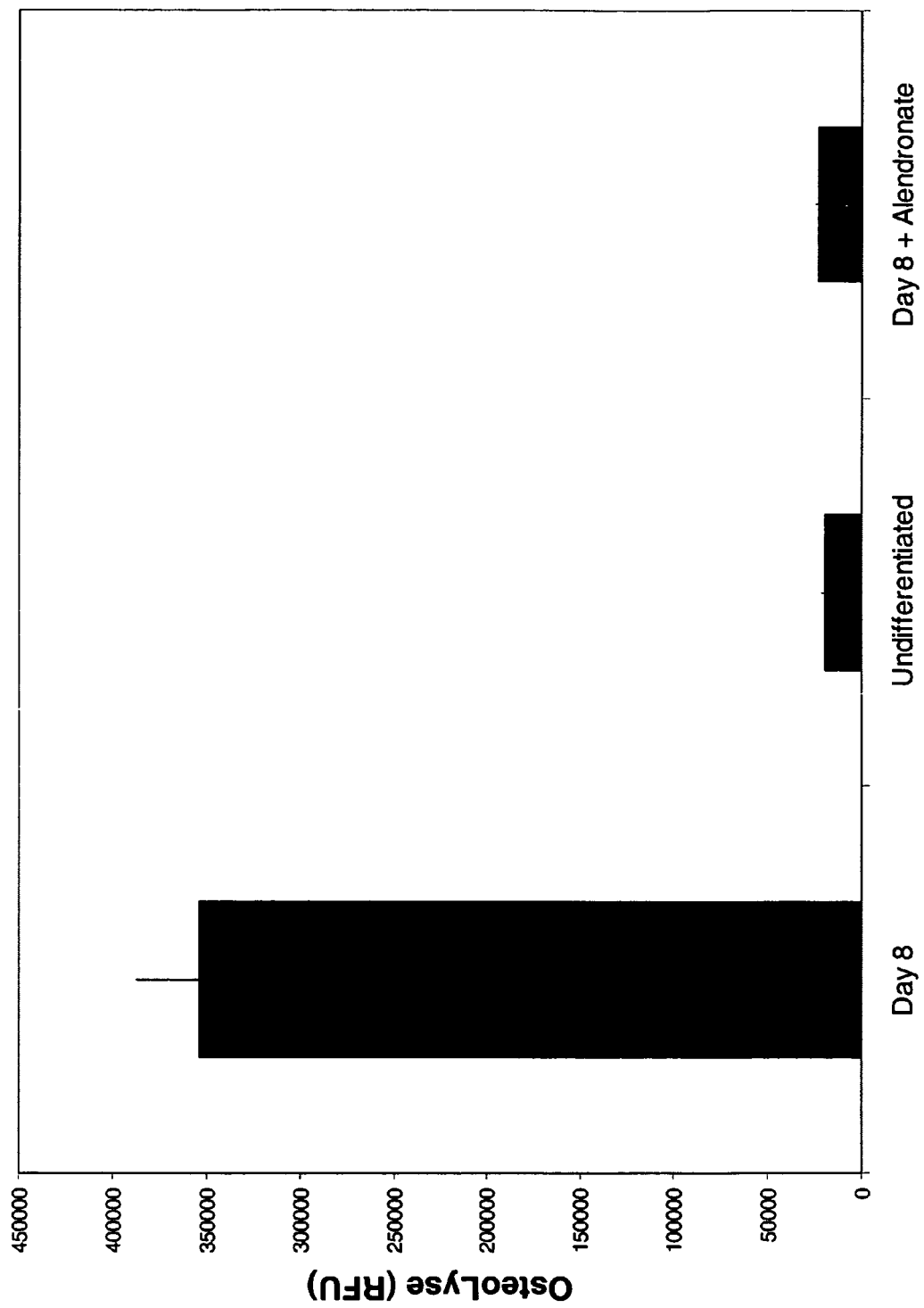
FIG. 7. Graph showing inhibition of in vitro bone matrix resorption by alendronate.

The media were renewed after 7 days. After an additional 24 hours, the cell culture media were sampled as described in Example 1. The results are shown in FIG. 7.

In another experiment, osteoclast precursors were cultured in differentiation medium with and without different concentrations of alendronate. After 7 days the media were renewed and, after an additional 3 days, the cell culture media were sampled as described in Example 1. Cells in the plate were subsequently stained for TRAP (Sigma # 386-A).

Figure 8:
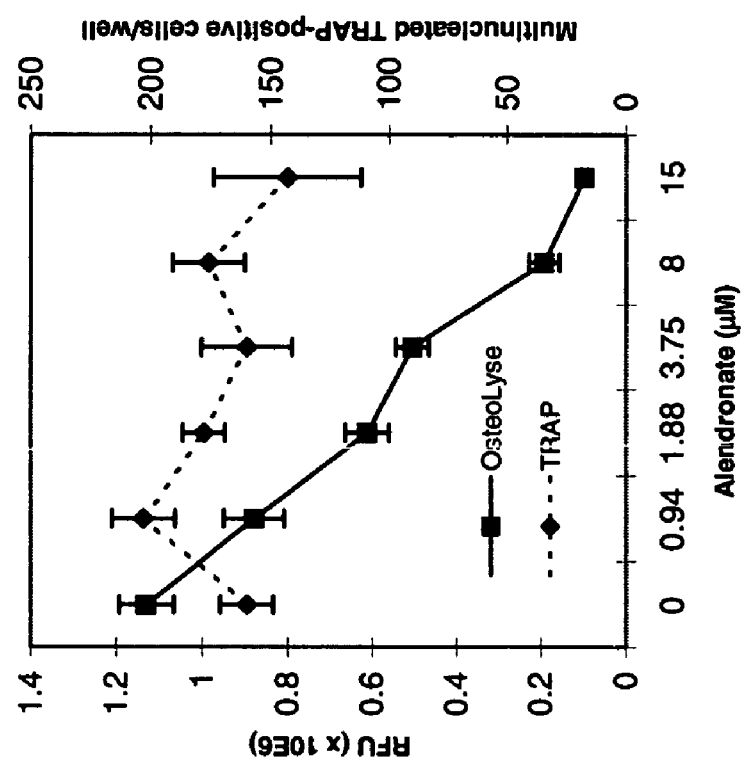
FIG. 8. Graph showing alendronate-mediated inhibition of in vitro bone matrix degradation by primary human osteoclasts as measured by OsteoLyse™ and TRAP assays.

The results are shown in FIG. 8. Alendronate did not inhibit the differentiation of the osteoclast precursors as measured by the presence of multinucleated TRAP-positive osteoclasts.

EXAMPLE 9

Figure 9:
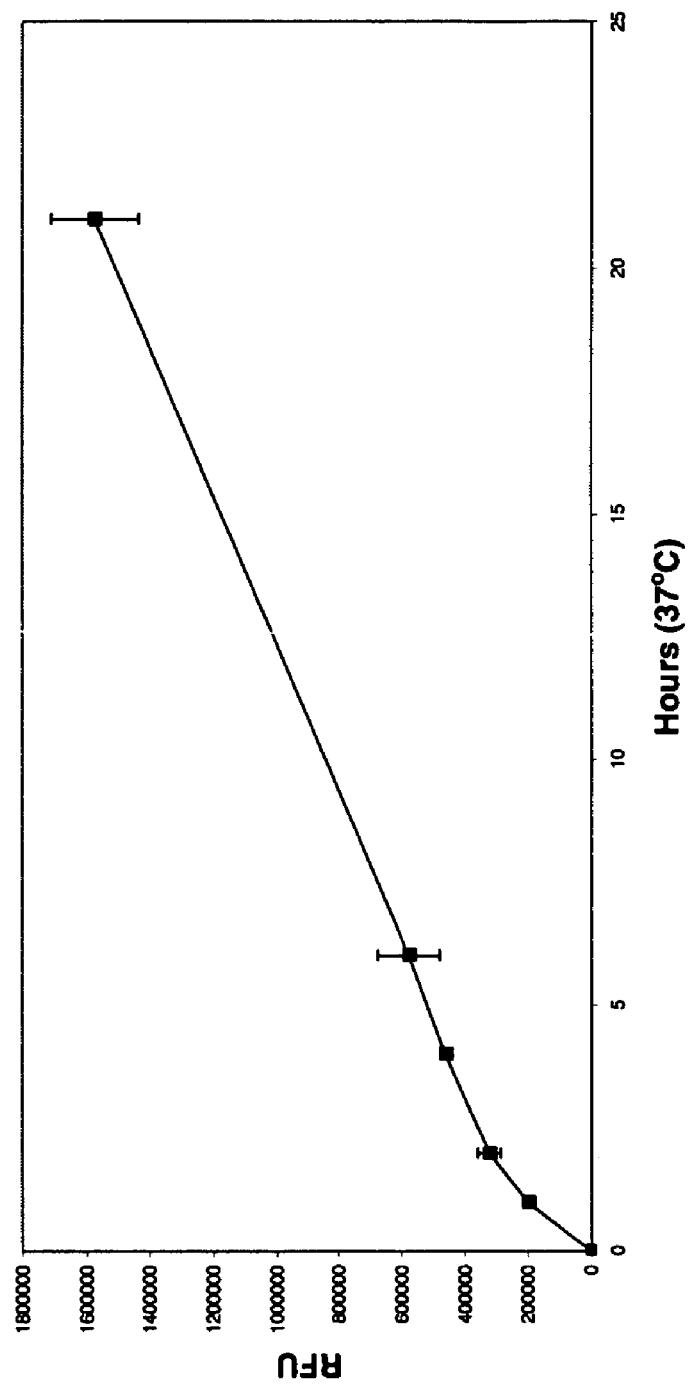
FIG. 9. Graph showing covalent binding of europium chelate-labeled collagen to maleic anhydride-derivatized polystyrene tissue culture plate over time.

Covalent Binding of Europium Chelate-Labeled Collagen to Maleic Anhydride-Derivatized Polystyrene Tissue Culture Plate Over Time Europium chelate-labeled human type I collagen was placed in the wells of a maleic anhydride-derivatized polystyrene tissue culture plate (50 μg/well) and incubated at 37° C. At various times, wells were aspirated and washed with detergent and 1 M sodium chloride to remove unbound collagen. Fluorophore Releasing Reagent (100 μl/well) was placed in each well and 1 μl/well was then withdrawn and diluted in 200 μl Fluorophore Releasing Reagent in a 96-well assay vessel. The fluorescence of each well was then determined. The results are shown in FIG. 9.

EXAMPLE 10

Release of Non-Covalently Bound Europium Chelate-Labeled Collagen Over Time

Europium chelate-labeled human type I collagen (at 55 μg/ml) was placed in the wells of a non-derivatized 96-well tissue culture plate (50 μl/well). The plate was then incubated at 37° C. for 2.5 hours. Excess collagen was removed and the wells were air-dried overnight. Each well was then rinsed with cell culture medium (200 μl/well) five times, filled with 200 μl medium and incubated at 37° C. for 24 hours. The medium was then sampled (5 μl) and each well rinsed 4 times with 200 μl medium. Each rinse was saved and sampled (5 μl).

The wells were then filled with medium (200 μl) and incubated for an additional 96 and 120 hours, after which the medium was sampled. The wells were then emptied and filled with 200 μl Fluorophore Releasing Reagent (DELFIA® Enhancement Solution), 5 μl of which was then sampled. Each 5 μl sample was diluted in 200 μl Fluorophore Releasing Reagent and counted.

Figure 10:
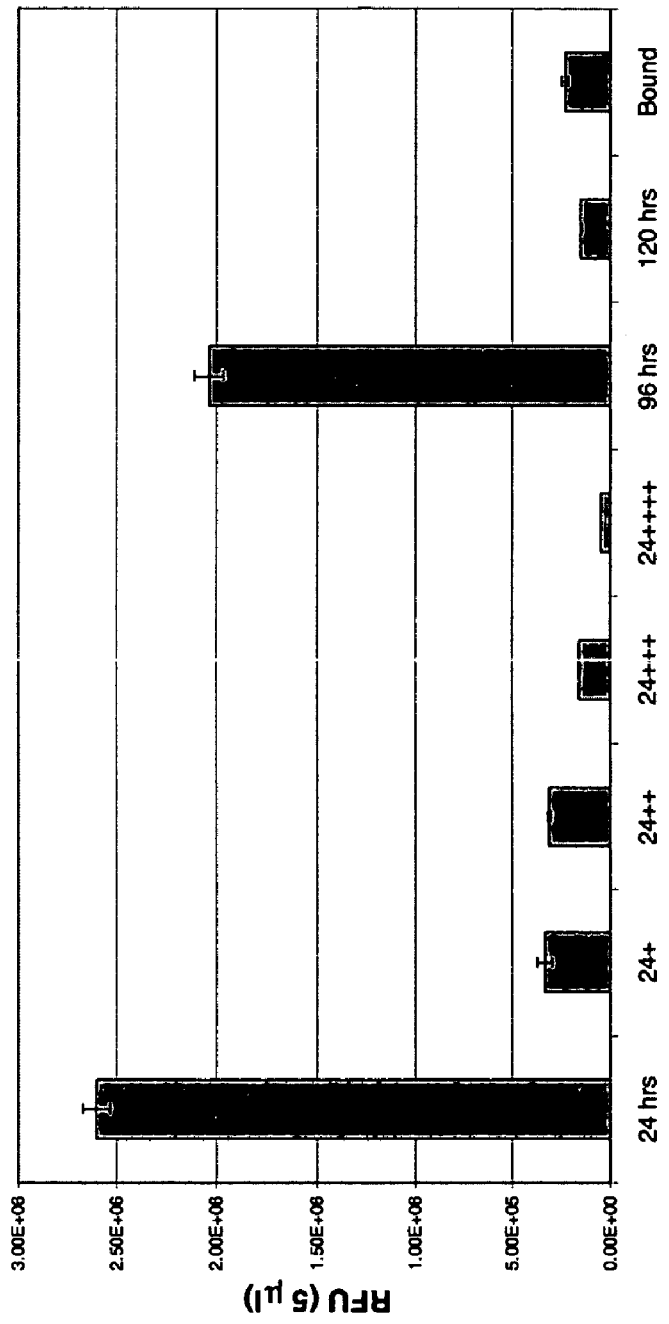
FIG. 10. Graph showing electrostatic collagen adherence to a Nunclon™Δ tissue culture plate.

The data show that less than 5% of the total europium chelate-labeled collagen remained attached to the plastic surface of the culture plate after 5 days of incubation. The results are shown in FIG. 10.

EXAMPLE 11

Demonstration of Apparent Molecular Masses of Europium Chelate-Labeled Collagen Degradation Fragments Osteoclast precursors were cultured on europium chelate-labeled collagen covalently bound to a maleic anhydride-derivatized polystyrene plate and differentiated as described in Example 2. After 7 days of culture, the medium was renewed and the culture continued. After 24 hours, culture media were combined, mixed with 100 μl of protein standards and loaded onto a 16 mm×600 mm Sephacryl-300 HD gel filtration column. The column was eluted with phosphate-buffered saline at 0.5 ml/minute. Three 150 ml fractions were collected, and 10 μl samples of each were counted in Fluorophore-Releasing Reagent (DELFIA® Enhancement Solution). The elution profile of the protein standards was determined by the absorbance of the fractions at 405 nm.

Figure 11:
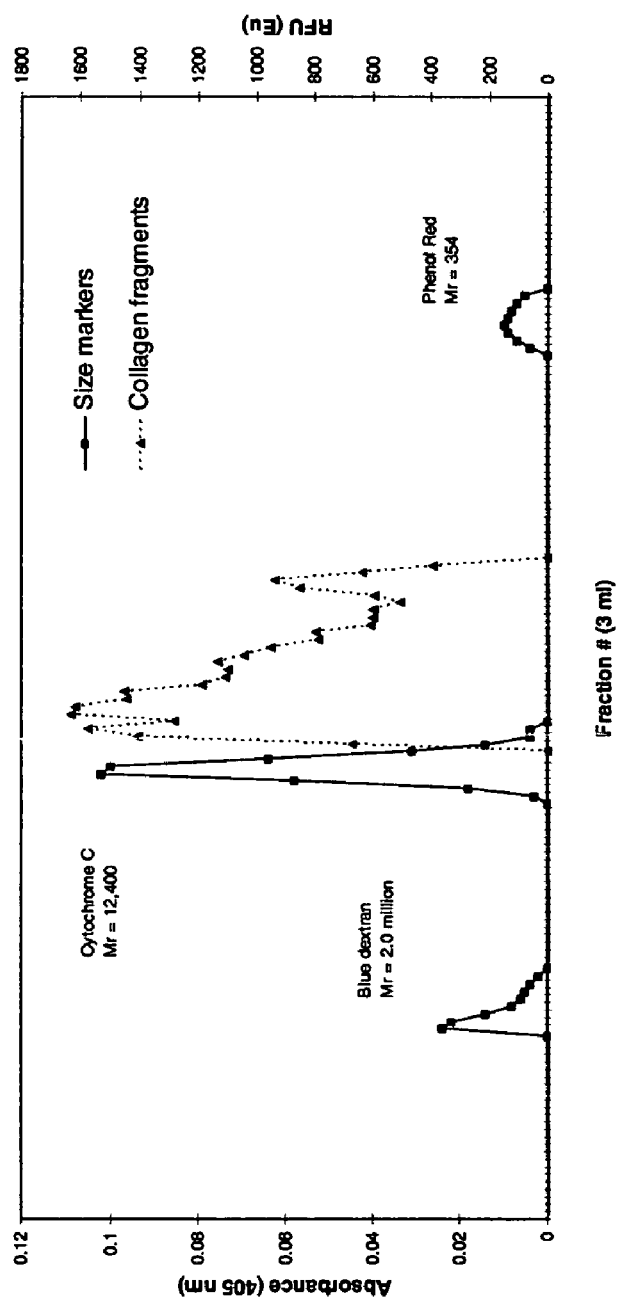
FIG. 11. Graph showing apparent molecular masses of europium chelate-labeled collagen degradation fragments.

The results show that europium chelate-labeled degradation fragments of collagen have apparent molecular masses of less than 12,000 daltons. See FIG. 11.

EXAMPLE 12

Release of Fluorophore-Labeled Collagen Fragments by Collagenase

Collagenase (type I, Worthington) was made up in DMEM cell culture medium and added to the wells of a maleic anhydride-derivatized polystyrene plate to which europium-labeled collagen (100 μl/well at 1 unit/ml) was covalently bound and incubated at 37° C. After 10, 20 and 30 minutes, 5 μl of the enzyme solution was added to 200 μl of Fluorophore-Releasing Reagent (DELFIA® Enhancement Solution) and counted.

Figure 12:
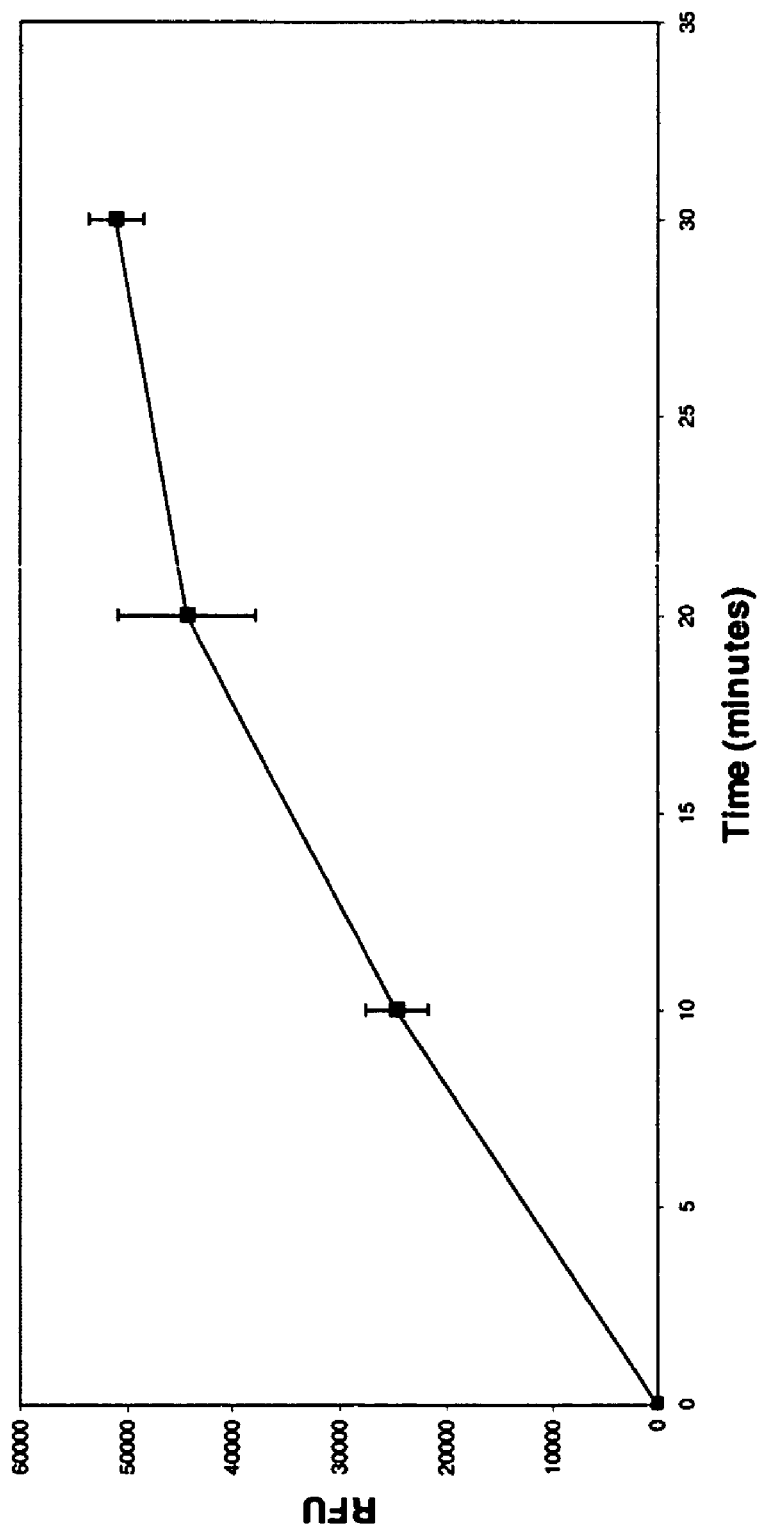
FIG. 12. Graph showing fluorescence resulting from release of europium chelate-labeled fragments by collagenase.

The results show that collagenase degradation of the covalently-bound collagen substrate released fluorophore-labeled fragments into the cell culture medium. See FIG. 12.

EXAMPLE 13

Osteoclast-Mediated Degradation of FITC-Labeled Collagen

FITC-labeled bovine type I collagen (DQ collagen, Molecular Probes, Inc.) was covalently bound to the surface of a maleic anhydride-derivatized 96-well tissue culture plate. Osteoclast precursors were cultured, with and without differentiation, in the plate as described in Example 2. Interferon γ (1 ng/ml) was added to some wells. At days 5, 7 and 9 of culture, 10 μl samples of each well were collected and added to 200 μl phosphate-buffered saline and counted in a fluorimeter (485/535 nm).

Figure 13:
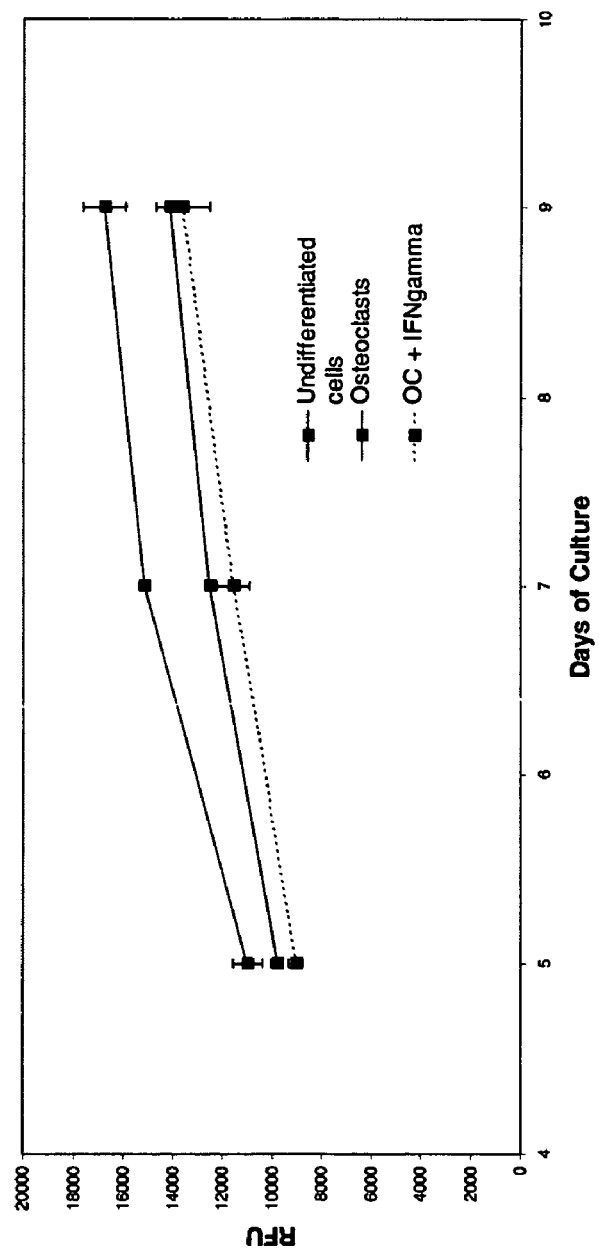
FIG. 13. Graph showing osteoclast-mediated degradation of FITC-labeled collagen over time.

The results are shown in FIG. 13. There was a statistical difference between the undifferentiated and differentiated cells. Interferon γ completely inhibited osteoclast-mediated collagen degradation. However, the absolute number of RFU was very low and the S:N ratio was close to 1. A likely explanation for this unsuitability is that the heavy fluorescein labeling renders the DQ collagen's free amino groups unavailable for binding to the cell culture surface of a cell culture vessel.

EXAMPLE 14

Unsuitability of Soluble DQ Collagen in a Cell-Based Collagen Degradation Assay

Osteoclast precursors were cultured with and without differentiation in a plastic 96-well tissue culture plate as described in Example 2. At day 0, soluble DQ FITC-labeled collagen (Molecular Probes, Inc.) was added to the cultures (1 μg/well).

After 9 days of culture, samples of the media (10 μl) were added to 200 μl phosphate-buffered saline and counted in a fluorimeter (485/535 nm).

Figure 14:
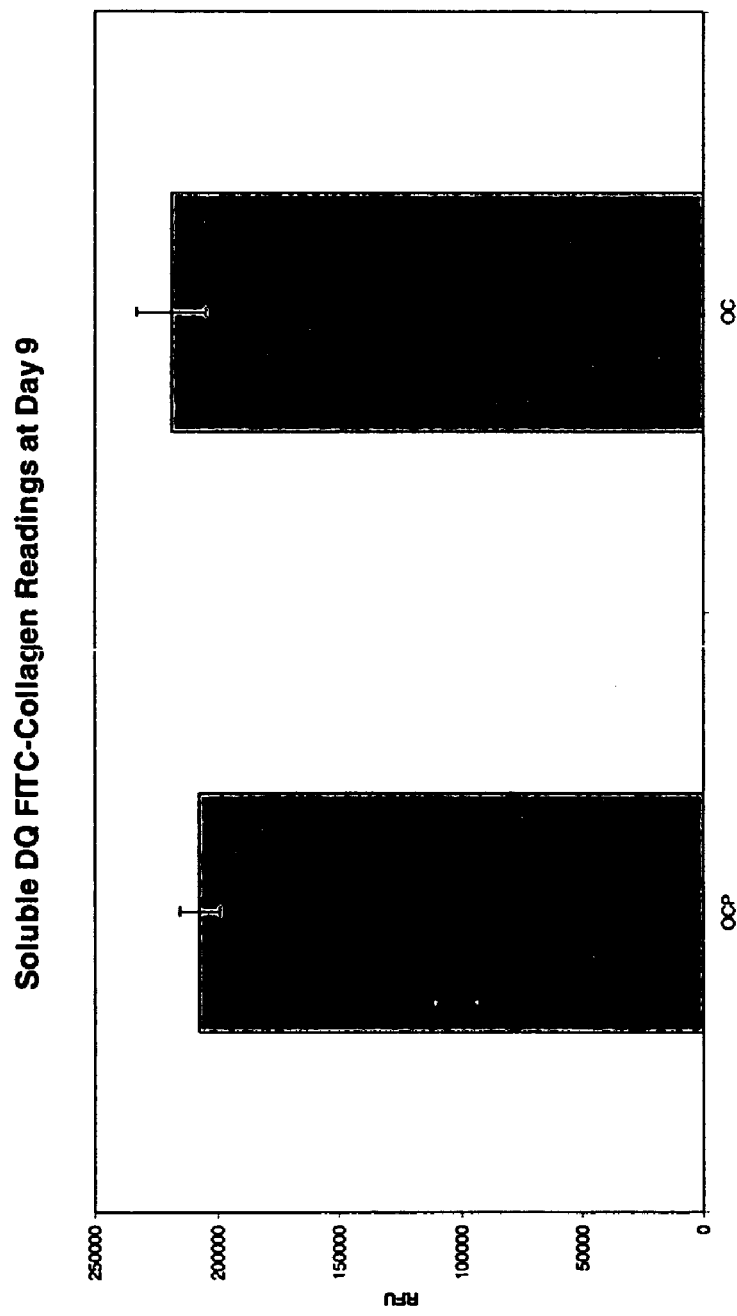
FIG. 14. Graph showing fluorescence readings for cell culture medium samples from osteoclast precursors cultured with soluble DQ FITC-labeled collagen for 9 days. OCTP, osteoclast precursors; OC, osteoclasts.

The results are shown in FIG. 14. There was no statistically significant difference in the relative fluorescence units (RFU) between differentiated and undifferentiated cells. These results demonstrate that soluble DQ collagen is not suitable for use in cell-based collagen degradation assays of the invention. A likely explanation for this unsuitability is that fluorescently labeled collagen substrate must be attached to the cell culture surface of the cell culture vessel. A mature osteoclast forms a "resorption lacuna" or "bay" at the basal side of the cell, which is separated from the cell culture medium and into which proteolytic enzymes are secreted. Collagen in the supernatant would not be available to these enzymes.

EXAMPLE 15

Osteoclast-Mediated Degradation of DQ Collagen in a One-Step Assay

Primary human osteoclast precursors (Cambrex product # 2T-110) are seeded onto DQ collagen covalently bound via stable thioester linkages to a maleimide-derivatized polystyrene plate (Pierce Reacti-Bind™) at 10,000 cells per well and cultured in medium containing M-CSF and soluble RANK ligand, as described in Example 2.

After 7 days of culture, the tissue culture plate is read in a fluorimeter (485/535 nm). The fluorescence read-out is due solely to fluorophore-labeled collagen fragments. This is because fluorescence of the covalently bound DQ collagen is quenched due to the heavy labeling density (i.e., the close proximity of one fluorescein molecule to another). Thus, the fluorescence signal in the cell culture medium in the wells of the tissue culture plate is directly proportional to the resorptive activity of mature osteoclasts.

EXAMPLE 16

Assay of Collagen I Degradation by Metastatic Tumor Cells

Figure 15:
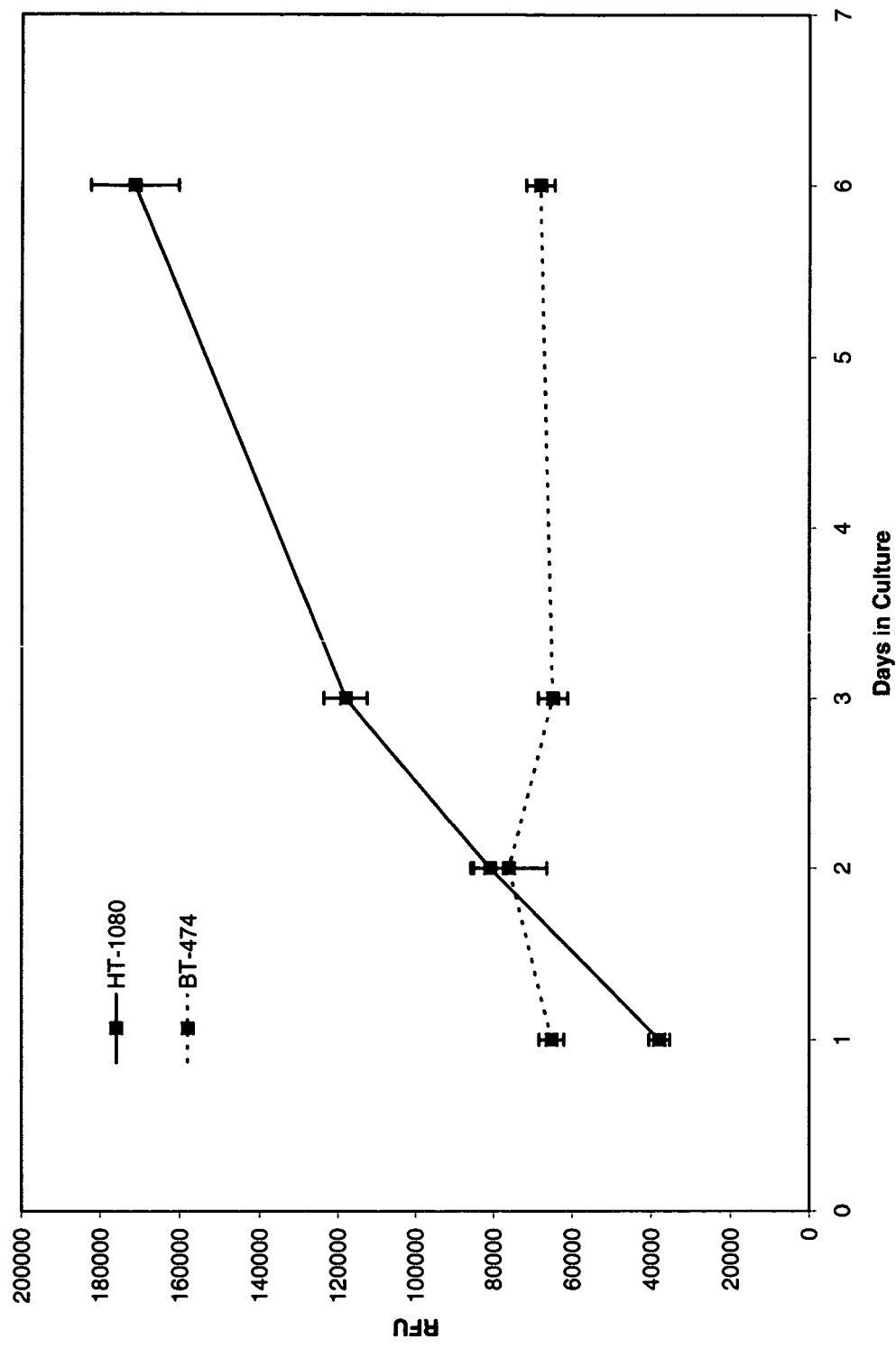
FIG. 15. Graph showing time course of human collagen type I degradation by human tumor cell lines.

Two cancer cell lines (HT-1080, which has been shown to be highly metastatic, and BT-474, which has been shown to be less metastatic) were seeded onto europium chelate-labeled collagen covalently bound to a maleic anhydride-derivatized polystyrene plate at 10,000 cells/well and cultured at 37° C. Every 24 hours, 10 µl of the cell culture medium were collected and counted in a 96-well plate containing 200 µl of Fluorophore-Releasing Reagent (DELFIA® Enhancement Solution). The results are shown in FIG. 15.

While the invention has been described in conjunction with specific embodiments, the description and examples above are intended to illustrate, but not limit the scope of the invention. This application is intended to cover those changes and substitutions that may be made by those skilled in the art without departing from the spirit and the scope of the invention. Other aspects, advantages and modifications will be apparent to those skilled in the art to which the invention pertains, and these aspects and modifications are within the scope of the invention, which is limited only by the appended claims.

The invention claimed is:

1. A method of detecting collagen degradation, comprising the steps of:
   (a) culturing cells in culture medium on fluorophore-labeled collagen covalently bound to a culture surface of a cell culture vessel, wherein the cells can degrade the collagen or can differentiate into cells which can degrade the collagen;
   (b) detecting the presence or absence of a fluorescence signal in a sample of the culture medium, wherein fluorescence signal intensity reflects the concentration of fluorophore-labeled collagen fragments in the sample of the culture medium.

2. The method of claim 1 further comprising the step of transferring the sample of the culture medium from the cell culture vessel to an assay vessel before the step of detecting.

3. The method of claim 2 wherein the fluorophore is a lanthanide chelate and wherein the assay vessel contains an enhancing solution.

4. The method of claim 3 wherein the lanthanide chelate is a europium chelate.

5. The method of claim 4 wherein the europium chelate is $Eu^{3+}$-N'-(p-isothiocyanatobenzyl) diethylenetriamine-$N^1$, $N^2$,$N^3$-tetraacetic acid.

6. The method of claim 1 wherein fluorescence of the covalently bound fluorophore-labeled collagen is quenched and wherein the step of detecting takes place in the cell culture vessel.

7. The method of claim 1 further comprising the step of testing an effect of a test compound on the collagen degradation by contacting the cells with the test compound before the step of detecting.

8. The method of claim 1 wherein the collagen is type I.

9. The method of claim 1 wherein the collagen is type IV.

10. The method of claim 1 wherein the collagen is mammalian.

11. The method of claim 1 wherein the collagen is human.

12. The method of claim 1 wherein the cells are human.

13. The method of claim 1 wherein the cells are osteoclasts.

14. The method of claim 1 wherein cells are osteoclast precursors.

15. The method of claim 1 wherein the cells are tumor cells.

16. A method of detecting collagen degradation, comprising the steps of:
   (a) culturing cells selected from the group consisting of osteoclasts and osteoclast precursors in culture medium on europium chelate-labeled human collagen type I covalently bound to a culture surface of a cell culture vessel;
   (b) transferring a sample of the culture medium from the cell culture vessel to an assay vessel; and
   (c) detecting the presence or absence of a fluorescence signal in the assay vessel, wherein fluorescence signal intensity reflects the concentration of europium chelate-labeled collagen fragments in the sample of the culture medium.

17. The method of claim 16 further comprising the step of testing an effect of a test on the collagen degradation by contacting the cells with the test compound before the step of transferring.

18. The method of claim 16 wherein the europium chelate is $Eu^{3+}$-N'-(p-isothiocyanatobenzyl) diethylenetriamine-$N^1$, $N^2$,$N^3$-tetraacetic acid.

19. The method of claim 16 wherein the cells are human osteoclast precursors.

20. A method of detecting collagen degradation, comprising the steps of:
   (a) culturing human osteoclasts in culture medium on europium chelate-labeled human collagen type I covalently bound to a culture surface of a cell culture vessel, wherein the europium chelate is $Eu^{3+}$-N'-(p-isothiocyanatobenzyl) diethylenetriamine-$N^1$,$N^2$, $N^3$-tetraacetic acid;
   (b) transferring a sample of the culture medium from the cell culture vessel to an assay vessel; and
   (c) detecting the presence or absence of a fluorescence signal in the assay vessel, wherein fluorescence signal intensity reflects the concentration of europium chelate-labeled collagen fragments in the sample of the culture medium.

* * * * *